(12) United States Patent
Neumann

(10) Patent No.: US 10,847,261 B1
(45) Date of Patent: Nov. 24, 2020

(54) METHODS AND SYSTEMS FOR PRIORITIZING COMPREHENSIVE DIAGNOSES

(71) Applicant: Kenneth Neumann, Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 0 days.

(21) Appl. No.: 16/668,423

(22) Filed: Oct. 30, 2019

(51) Int. Cl.
| | | |
|---|---|---|
| *G16H 20/00* | (2018.01) | |
| *G16H 10/60* | (2018.01) | |
| *G16H 50/30* | (2018.01) | |
| *G16H 70/60* | (2018.01) | |
| *G16H 50/20* | (2018.01) | |

(52) U.S. Cl.
CPC .......... *G16H 20/00* (2018.01); *G16H 10/60* (2018.01); *G16H 50/20* (2018.01); *G16H 50/30* (2018.01); *G16H 70/60* (2018.01)

(58) Field of Classification Search
CPC ........ G16H 20/00; G16H 70/60; G16H 10/60; G16H 50/30; G16H 50/20
See application file for complete search history.

(56) References Cited

U.S. PATENT DOCUMENTS

| | | | |
|---|---|---|---|
| 10,332,631 B2 | 6/2019 | Miller et al. | |
| 2004/0122709 A1* | 6/2004 | Avinash | G06F 19/3418 705/2 |
| 2008/0195594 A1 | 8/2008 | Gerjets | |
| 2014/0058742 A1* | 2/2014 | Chari | G16H 50/20 705/2 |
| 2014/0343961 A1 | 11/2014 | Thesman | |
| 2015/0120319 A1 | 4/2015 | Wilson | |
| 2015/0199782 A1* | 7/2015 | Reddy | G06Q 50/22 705/2 |
| 2016/0098542 A1 | 4/2016 | Costantini et al. | |
| 2016/0232310 A1 | 8/2016 | Dunn et al. | |
| 2018/0011980 A1 | 1/2018 | Contu et al. | |
| 2018/0102190 A1* | 4/2018 | Hogue | G16H 10/60 |
| 2019/0065687 A1* | 2/2019 | Mei | G06F 19/325 |
| 2019/0087727 A1 | 3/2019 | Skellenger | |
| 2019/0130069 A1 | 5/2019 | Li et al. | |
| 2019/0311814 A1* | 10/2019 | Kannan | G16H 80/00 |
| 2019/0367968 A1* | 12/2019 | Apte | C12Q 1/689 |

* cited by examiner

*Primary Examiner* — Fonya M Long
*Assistant Examiner* — Anthony Michael Balaj
(74) *Attorney, Agent, or Firm* — Caldwell Intellectual Propert

(57) ABSTRACT

A system for prioritizing comprehensive diagnoses includes a classification module. The classification module is configured to receive a user identifier entered by a comprehensive advisor located on a graphical user interface operating on a processor, retrieve a user biological marker from a biological marker database, receive classification training data, generate a naïve Bayes classification algorithm utilizing the classification training data to output a biological marker classification label. The system includes a priority treatment module. The priority treatment module is configured to receive a plurality of user comprehensive diagnoses, select a treatment training set, generate using a supervised machine-learning model a treatment model, evaluate one or more prioritized treatment facets, generate a treatment instruction set, and display the treatment instruction set on a graphical user interface.

20 Claims, 12 Drawing Sheets

| | Biological Marker | Sample Type | Reading | Reference Range | Alert Status | Sex | Age |
|---|---|---|---|---|---|---|---|
| 1 | Cortisol | Saliva | 0.2 mcg/dL | 0.097-0.337 mcg/dL | Non-Alert | Male | 22 |
| 2 | Bisphenol A | Urine | 10.44 mcg/gm | 0-1.95 mcg/gm | Alert | Male | 59 |
| 3 | Pancreatic Elastase | Stool | 167 mcg/g | Greater than 200 mcg/g | Alert | Female | 82 |
| 4 | Enterobacter Cloacae | Stool | 4 SD | 0-2 SD | Alert | Male | 57 |
| 5 | Estrone Sulfate | Plasma | 2.18 ng/mL | 0.56-2.67 ng/mL | Non-Alert | Female | 34 |
| 6 | Zonulin Family Peptide | Serum | 65.2 ng/mL | 25.5-56.1 ng/mL | Alert | Female | 19 |
| 7 | Methane | Breath | 17 ppm | 0-19 ppm | Non-Alert | Female | 44 |
| 8 | Glucose | Cerebrospinal fluid | 107 mg/dL | 45-80 mg/dL | Alert | Male | 38 |
| 9 | DHEA-S | Plasma | 91 mcg/dL | 35-430 mcg/dL | Non-Alert | Female | 51 |
| 10 | Lead | Hair | 55 ppm | 0-12 ppm | Alert | Male | 29 |

FIG. 5A

| Comprehensive Diagnosis | First Prioritized Treatment Facet | Second Prioritized Treatment Facet | Third Prioritized Treatment Facet | Fourth Prioritized Treatment Facet | Fifth Prioritized Treatment Facet | Nth Prioritized Treatment Facet |
|---|---|---|---|---|---|---|
| 1 Rheumatoid Arthritis | Initiate gluten free diet | Heal the gut | Find and treat infections | Test for heavy metals | Test for mycotoxins | Support the immune system |
| 2 Sinus Infection | Initiate probiotic regimen | Modify biofilm | Address viral infections | Address environmental toxins | Balance immune systems | |
| 3 Acid Reflux | Initiate low acid diet | Eliminate food allergies | Eliminate trigger foods | Start meditation practice | | |
| 4 Irritable Bowel Syndrome | Initiate glutamine supplement regimen | Take herbal anti-microbial regimen | Consume low FODMAP diet | | | |
| 5 Low Back Pain | Initiate chriopractic adjustment | Participate in cognitive behavioral therapy | Strat yoga practice | | | |

FIG. 9

METHODS AND SYSTEMS FOR PRIORITIZING COMPREHENSIVE DIAGNOSES

FIELD OF THE INVENTION

The present invention generally relates to the field of artificial intelligence. In particular, the present invention is directed to methods and systems for prioritizing comprehensive diagnoses.

BACKGROUND

Accurate selection and treatment of comprehensive diagnoses is imperative to achieve a vibrant constitution. Frequently, comprehensive advisors can get overwhelmed with the number of factors that are necessary to calculate and stay current on to accurately and efficiently prioritize comprehensive diagnoses. Unfortunately, many comprehensive diagnoses are left untreated due to a lack of understanding of current knowledge and guidelines.

SUMMARY OF THE DISCLOSURE

In an aspect, a system for prioritizing comprehensive diagnoses. The system includes a processor wherein the processor further comprises a classification module the classification module designed and configured to receive a user identifier entered by a comprehensive advisor located on a graphical user interface operating on the processor; retrieve a user biological marker from a biological marker database as a function of the user identifier; receive classification training data wherein the classification training data contains a plurality of data entries including biological marker data containing alert and non-alert classification labels; and generate a naïve Bayes classification algorithm utilizing classification training data wherein the naïve Bayes classification algorithm utilizes the user biological marker as an input and outputs a biological marker classification label. The system includes a priority treatment module the priority module designed and configured to receive the biological marker classification label from the classification module; receive a plurality of user comprehensive diagnoses entered by a comprehensive advisor on a graphical user interface operating on the processor; select a treatment training set as a function of the biological marker classification label wherein the treatment training set includes a plurality of data entries containing comprehensive diagnoses correlated to one or more prioritized treatment facets; generate using a supervised machine-learning model a treatment model that outputs an ordered priority treatment list for each of the plurality of comprehensive diagnoses utilizing the selected treatment training set; evaluate the one or more prioritized treatment facets contained within the ordered priority treatment list for the plurality of comprehensive diagnoses; generate a treatment instruction set wherein the treatment instruction set further comprises generating an ordered treatment plan containing one or more combined prioritized treatment facets for the plurality of comprehensive diagnoses; and display the treatment instruction set on a graphical user interface located on the processor.

In an aspect, a method of prioritizing comprehensive diagnoses. The method includes receiving by a processor a user identifier entered by a comprehensive advisor located on a graphical user interface operating on the processor. The method includes retrieving by the processor a user biological marker from a biological marker database as a function of the user identifier. The method includes receiving by the processor classification training data wherein the classification training data contains a plurality of data entries including biological marker data containing alert and non-alert classification labels. The method includes generating by the processor a naïve Bayes classification algorithm utilizing classification training data wherein the naïve Bayes classification algorithm utilizes the user biological marker as an input and outputs a biological marker classification label. The method includes receiving by the processor a plurality of user comprehensive diagnoses entered by a comprehensive advisor on a graphical user interface operating on the processor. The method includes selecting by the processor a treatment training set as a function of the biological marker classification label wherein the treatment training set includes a plurality of data entries containing comprehensive diagnoses correlated to one or more prioritized treatment facets. The method includes generating by the processor using a supervised machine-learning model a treatment model that outputs an ordered priority treatment list for each of the plurality of comprehensive diagnoses utilizing the selected treatment training set. The method includes evaluating by the processor the one or more prioritized treatment facets contained within the ordered priority treatment list for the plurality of comprehensive diagnoses. The method includes generating by the processor a treatment instruction set wherein the treatment instruction set further comprises generating an ordered treatment plan containing one or more combined prioritized treatment facets for the plurality of comprehensive diagnoses. The method includes displaying by the processor the treatment instruction set on a graphical user interface located on the processor.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5A-5B are a diagrammatic representation of classification training data;

FIG. 9 is a diagrammatic representation of treatment training set;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Figure 1:
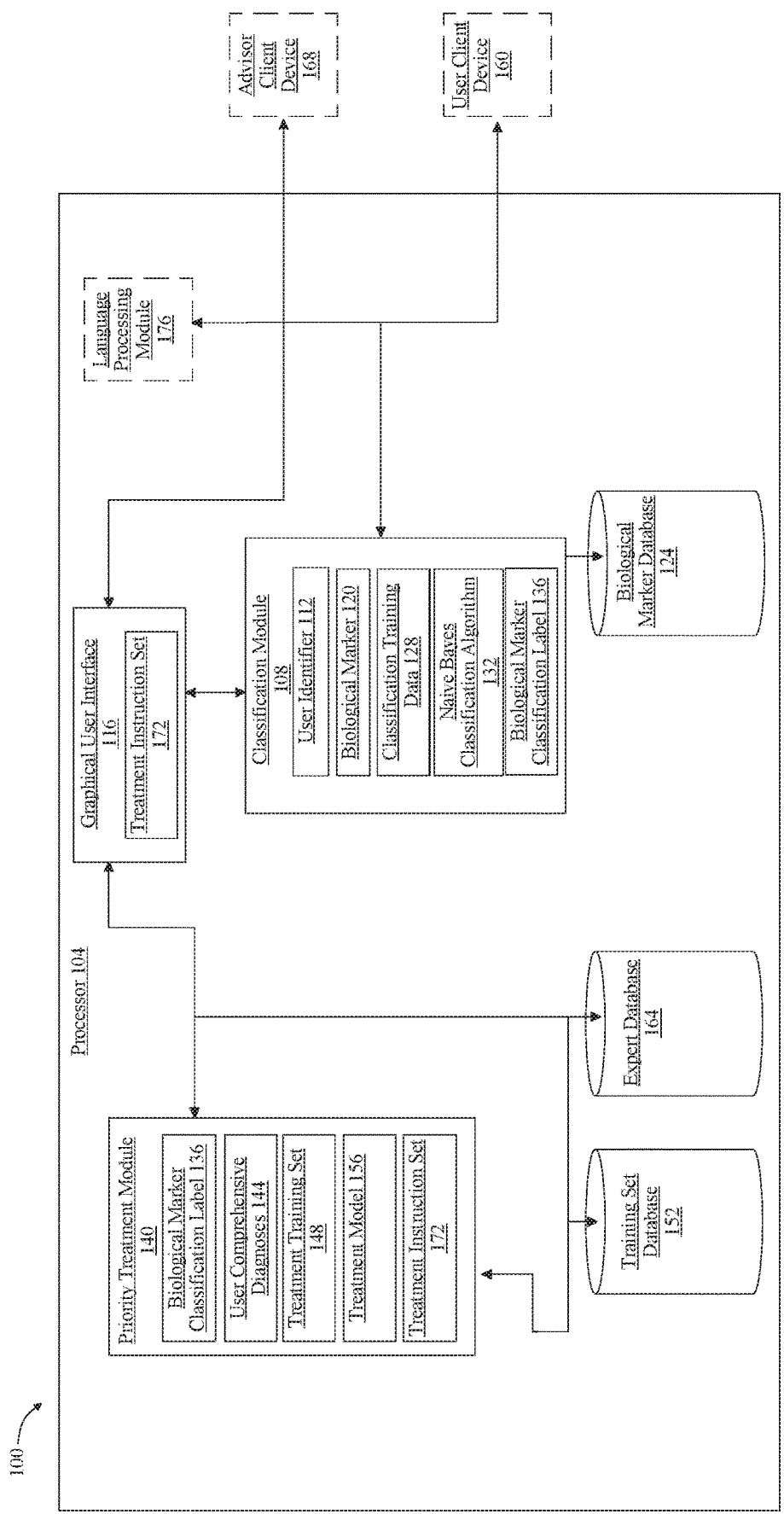
FIG. 1 is a block diagram illustrating an exemplary embodiment of a system for prioritizing comprehensive diagnoses.

Referring now to the drawings, FIG. 1 illustrates an exemplary embodiment of a system 100 for prioritizing comprehensive diagnoses. System 100 includes a processor. A processor 104 may include any computing device as described herein, including without limitation a microcontroller, microprocessor 104, digital signal processor 104 (DSP) and/or system on a chip (SoC) as described herein. A processor 104 may be housed with, may be incorporated in, or may incorporate one or more sensors of at least a sensor. Computing device may include, be included in, and/or communicate with a mobile device such as a mobile telephone or smartphone. A processor 104 may include a single computing device operating independently, or may include two or more computing device operating in concert, in parallel, sequentially or the like; two or more computing devices may be included together in a single computing device or in two or more computing devices. A processor 104 with one or more additional devices as described below in further detail via a network interface device. Network interface device may be utilized for connecting a processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. A processor 104 may include but is not limited to, for example, A processor 104 or cluster of computing devices in a first location and a second computing device or cluster of computing devices in a second location. A processor 104 may include one or more computing devices dedicated to data storage, security, distribution of traffic for load balancing, and the like. A processor 104 may distribute one or more computing tasks as described below across a plurality of computing devices of computing device, which may operate in parallel, in series, redundantly, or in any other manner used for distribution of tasks or memory between computing devices. A processor 104 may be implemented using a "shared nothing" architecture in which data is cached at the worker, in an embodiment, this may enable scalability of system 100 and/or computing device.

With continued reference to FIG. 1, a processor 104 may be designed and/or configured to perform any method, method step, or sequence of method steps in any embodiment described in this disclosure, in any order and with any degree of repetition. For instance, a processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a classification module 108 which may be implemented as any hardware and/or software module. Classification module 108 is designed and configured to receive a user identifier 112 entered by a comprehensive advisor located on a graphical user interface operating on a processor, retrieve a user biological marker 120 from a user database, receive classification training data wherein the classification training data contains a plurality of data entries including biological marker data containing alert and non-alert labels and generate a naïve Bayes classification algorithm utilizing classification training data wherein the naïve Bayes classification algorithm utilizes the user biological marker as an input and outputs a biological marker classification label.

With continued reference to FIG. 1, a "user identifier" as used in this disclosure, includes any data that uniquely identifies a particular user. Data may include a user's name, a user's date of birth, a user's medical identification number, a public and/or private key pair, a cryptographic hash, a biometric identifier such as an iris scan, fingerprint scan, a palm vein scan, a retina scan, facial recognition, DNA, a personal identification number, a driver's license or passport, token-based identification systems, digital signatures, and the like. Uniqueness may include uniqueness within system 100 such as ensuring that a particular user identifier is not already utilized by another user. Uniqueness may include a statistically ensured uniqueness such as a global unique identifier (GUID), or a unique identifier identification (UID).

With continued reference to FIG. 1, a user identifier 112 is entered by a comprehensive advisor. A "comprehensive advisor" as used in this disclosure, includes a person who is licensed by a state and/or federal licensing agency that may help in identifying, preventing, and/or treating illness and/or disability. A comprehensive advisor may include persons such as a functional medicine doctor, a doctor of osteopathy, a nurse practitioner, a physician assistant, a Doctor of Optometry, a doctor of dental medicine, a doctor of dental surgery, a naturopathic doctor, a doctor of physical therapy, a nurse, a doctor of chiropractic medicine, a doctor of oriental medicine and the like. A comprehensive advisor may include other skilled professionals such as nurses, respiratory therapists, pharmacists, home health aides, audiologists, clinical nurse specialists, nutritionists, dieticians, clinical psychologists, psychiatric mental health nurse practitioners, spiritual coaches, life coaches, holistic medicine specialists, acupuncturists, reiki masters, yoga instructors, holistic health coaches, wellness advisors and the like.

With continued reference to FIG. 1, a user identifier 112 is entered by a comprehensive advisor on a graphical user interface 116 operating on the processor. Graphical user interface may interact with a remote device such as a device in communication with system 1000 such as user client device and/or advisor client device through hypertext markup language (HTML) to be displayed on a remote device. In an embodiment, graphical user interface 116 may be displayed on a remote device as a web form. Graphical user interface 116 may include without limitation, a form or other graphical element having data entry fields, where a comprehensive advisor may enter a user identifier 112. Graphical user interface 116 may include data entry fields that allow for a comprehensive advisor to enter free form textual inputs. Graphical user interface 116 may provide drop-down lists, where users such as comprehensive advisors may be able to select one or more entries to indicate one or more users. Graphical user interface 116 may include touch options where a user may enter a command by touching and selecting a particular option. Graphical user interface 116 may include text to speech software whereby a comprehensive advisor may speak a particular command such as a user identifier 112 and graphical user interface 116 may convert the spoken command into a textual output that is displayed on graphical user interface 116.

With continued reference to FIG. 1, a "biological marker" as used in this disclosure, includes a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological marker 120 may include at least a genetic sample. At least a genetic sample may include a complete genome of a person or any portion thereof. At least a genetic sample may include a DNA sample and/or an RNA sample. At least a biological marker 120 may include an epigenetic sample, a proteomic sample, a tissue sample, a biopsy, and/or any other physically extracted sample. At least a biological marker 120 may include an endocrinal sample. As a further non-limiting example, the at least a biological marker 120 may include a signal from at least a sensor configured to detect physiological data of a user and recording the at least a biological marker 120 as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensor, magnetoencephalographic sensor, electrocardiographic sensor, electromyographic sensor, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, blood sugar, and/or blood pressure. At least a sensor may be configured to detect internal and/or external biomarkers and/or readings. At least a sensor may be a part of system 100 or may be a separate device in communication with system 100.

Still referring to FIG. 1, at least a biological marker 120 may include any result of any medical test, physiological assessment, cognitive assessment, psychological assessment, or the like. System 100 may receive at least a biological marker 120 from one or more other devices after performance; system 100 may alternatively or additionally perform one or more assessments and/or tests to obtain at least a biological marker 120, and/or one or more portions thereof, on system 100. For instance, at least biological marker 120 may include or more entries by a user in a form or similar graphical user interface 116 object; one or more entries may include, without limitation, user responses to questions on a psychological, behavioral, personality, or cognitive test. For instance, a processor may present to user a set of assessment questions designed or intended to evaluate a current state of mind of the user, a current psychological state of the user, a personality trait of the user, or the like; a processor may provide user-entered responses to such questions directly as at least a biological marker 120 and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological marker 120 may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological marker 120 may include data describing one or more test results, including results of mobility tests, stress tests, dexterity tests, endocrinal tests, genetic tests, and/or electromyographic tests, biopsies, radiological tests, genetic tests, and/or sensor tests. Persons skilled in the art, upon reviewing the entirety of this disclosure, will be aware of various additional examples of at least a physiological sample consistent with this disclosure.

With continued reference to FIG. 1, a user biological marker 120 may be stored in a user biological marker database 124. Biological marker includes any of the biological markers as described above. Biological marker database 124 may be implemented, without limitation, as a relational database, a key-value retrieval datastore such as a NOSQL database, or any other format or structure for use as a datastore that a person skilled in the art would recognize as suitable upon review of the entirety of this disclosure. Biological marker database 124 may include one or more data entries containing one or more user biological marker 120. Processor may select one or more user biological marker 120 from biological marker database 124 by evaluating a user identifier 112 entered by a comprehensive advisor on a graphical user interface 116 to a user identifier 112 located within biological marker database 124. In an embodiment, each biological marker 120 contained within biological marker database 124 may contain an individual user identifier 112. A processor may evaluate biological marker 120 by comparing user identifier 112 to determine if they are identical and belong to the same user. For instance and without limitation, a processor may evaluate a user identifier 112 generated by a comprehensive advisor on a graphical user interface 116 that includes a user's name and date of birth to a user identifier 112 contained within biological marker database 124 that includes a user's name and date of birth. In such an instance, processor may evaluate both usernames and dates of birth to determine if they are identical and match. Evaluating may include other techniques such as comparing hash values and authenticating public and private key pairs. Processor may continue to retrieve a user biological marker 120 from biological marker database 124 after confirming that user identifier 112 match. In an embodiment, processor may not proceed to retrieve a user biological marker 120 from a biological marker database 124 when user identifier 112 do not match.

With continued reference to FIG. 1, classification module 108 is configured to receive classification training data 128. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server may correlate any input data as described in this disclosure to any output data as described in this disclosure.

With continued reference to FIG. 1, classification training data 128 includes a plurality of data entries including biological marker 120 data containing alert and non-alert classification labels. Biological marker 120 data includes any of the biological marker 120 data as described above. A "classification label" as used in this disclosure, includes an indicator that a particular data entry belongs to a specific class based on a common property and/or attribute. Classification training data 128 contains observations whose category membership or classification labels are already known. Classification labels are generated by classification algorithms. Classification algorithms may include generating classifications models that draws a conclusion from input values given for training data. Classification algorithms predict classification labels for new data. Classification training data 128 includes biological marker 120 data containing alert and non-alert classification labels. An "alert classification label" as used in this disclosure, includes an indicator that a particular biological marker 120 represents an alert condition. An alert condition includes an instance where a particular biological marker 120 is outside of normal reference ranges, indicates a potentially life threatening condition, indicates abnormal findings, indicates the need for immediate medical attention, and the like. For instance and without limitation, a biological marker 120 such as a serum sodium level of 155 mEq/L may be classified to contain an alert classification label when compared to a reference range of serum sodium levels between 135 and 145 mEq/L. A "non-alert classification label" as used in this disclosure, includes an indicator that a particular biological marker 120 does not contain an alert condition. A non-alert condition includes an instance where a particular biological marker 120 is within normal reference ranges, does not indicate a potentially life threatening condition, indicates normal findings, does not indicate the need for immediate medical attention and the like. For instance and without limitation, a biological marker 120 such as an electroencephalography (EEG) that contains no abnormal findings may be classified to contain a non-alert classification label.

With continued reference to FIG. 1, classification module 108 is configured to generate a naïve Bayes classification algorithm 132. Naïve Bayes classification algorithm generates classifiers by assigning class labels to problem instances, represented as vectors of feature values. Class labels are drawn from a finite set. Naïve Bayes classification algorithm may include generating a family of algorithms that assume that the value of a particular feature is independent of the value of any other feature, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming classification training data 128 into a frequency table. Classification module 108 may then calculate a likelihood table by calculating probabilities of different data entries and classification labels. Classification module 108 utilizes a naïve Bayes equation to calculate a posterior probability for each class. A class containing the highest posterior probability is the outcome of prediction. Naïve Bayes classification algorithm 132 may include a gaussian model that follows a normal distribution. Naïve Bayes classification algorithm may include a multinomial model that is used for discrete counts. Naïve Bayes classification algorithm 132 may include a Bernoulli model that may be utilized when feature vectors are binary. Naïve Bayes classification algorithm 132 utilizes classification training data 128 and a user biological marker 120 as an input to output a biological marker classification label 136. A "biological marker classification label 136" as used in this disclosure, includes a classification label generated for a user biological marker 120. A classification label includes an identifying that indicates whether a particular biological marker 120 belongs to a particular class or not. In an embodiment, a biological marker classification label 136 may include an alert or a non-alert classification label. In an embodiment, a biological marker classification label 136 may include other classification labels such as classification labels that may indicate progression of a particular disease, progression of a particular treatment and the like.

With continued reference to FIG. 1, classification module 108 may be configured to perform classification utilizing one or more other classification algorithms. Classification algorithms include but are not limited to logistic regression, fisher's linear discriminant, least squares support vector machines, quadratic classifiers, k-nearest neighbor, support vector machines, decision trees, boosted trees, random forest, neural networks, learning vector quantization and the like.

With continued reference to FIG. 1, system 100 includes a priority treatment module 140 which may be implemented as any hardware and/or software module. Priority treatment module 140 is designed and configured to receive the biological marker classification label 136 from the classification module 108; receive a plurality of user comprehensive diagnoses 144 generated by a comprehensive advisor on a graphical user interface 116 operating on the processor; select a treatment training set 148 as a function of the biological marker classification label 136 wherein the treatment training set 148 correlates comprehensive diagnoses to prioritized treatment facets; generate using a supervised machine-learning model a treatment model 156 that outputs an ordered priority treatment list for each of the plurality of comprehensive diagnoses utilizing the selected treatment training set; evaluate the priority treatment for each of the plurality of comprehensive diagnoses; generate a treatment instruction set 172 wherein the treatment instruction set 172 further comprises generating an ordered treatment plan for the plurality of comprehensive diagnoses; and display the ordered treatment instruction set 172 on a graphical user interface 116 located on the processor.

With continued reference to FIG. 1, priority treatment module 140 is configured to receive a plurality of user comprehensive diagnoses 144 generated by a comprehensive advisor on a graphical user interface 116 operating on a processor. A "comprehensive diagnosis" as used in this disclosure, includes a disease and/or condition diagnosed by a comprehensive advisor. A comprehensive diagnosis may explain particular signs and symptoms experienced by a user. A comprehensive diagnosis may be generated from information gathered from a medical history, physical examination, one or more diagnostic procedures such as medical tests, and one or more biological marker 120. For instance and without limitation, a comprehensive advisor such as a functional medicine doctor may diagnose a user with a comprehensive diagnosis of lupus after user complains of symptoms that include achy joints, unexplained fever, skin rash, and a butterfly shaped rash across user's cheeks and nose. In such an instance, comprehensive advisor may base a lupus diagnosis on user's symptoms and on medical tests such as blood and urine tests, antinuclear antibody (ANA) tests and the like. A "plurality of user comprehensive diagnoses" as used in this disclosure, includes one or more comprehensive diagnoses pertaining to a particular user. For example, a plurality of user comprehensive diagnoses may include estrogen dominance, back spasm, tinnitus, and sinus infection all of which may pertain to the same user and all of which may have been diagnosed by one or more comprehensive advisors.

With continued reference to FIG. 1, a plurality of user comprehensive diagnoses 144 are entered by a comprehensive advisor on a graphical user interface 116 operating on a processor. Graphical user interface 116 may include any of the graphical user interface 116 as described above. In an embodiment, a comprehensive advisor may enter into a free form text box one or more comprehensive diagnoses. In an embodiment, comprehensive advisor may enter a user identifier 112 whereby a list of comprehensive diagnoses associated with a user may be generated and displayed on a graphical user interface 116 so that comprehensive advisor may select one or more comprehensive diagnoses. In an embodiment, one or more comprehensive diagnoses may be retrieved from user database as described in more detail below.

With continued reference to FIG. 1, system 100 may include user database. User database may be implemented as any data structure suitable for use as biological marker database 124 as described above. User database may include one or more data entries containing information relevant to a particular user. For instance and without limitation, user database may include one or more comprehensive diagnoses. In yet another non-limiting example, user database may include one or more meeting summaries from an appointment with a comprehensive advisor. User database is described in more detail below.

With continued reference to FIG. 1, priority treatment module 140 selects a treatment training set 148 as a function of a biological marker classification label 136. Treatment training set includes any of the training data as described above. Treatment training set contains a plurality of data entries containing comprehensive diagnoses correlated to one or more prioritized treatment facets. "Prioritized treatment facet" as used in this disclosure, includes a treatment plan for a particular diagnosis that indicates what aspect of the particular diagnosis needs to be treated first, what needs to be treated next and what needs to be addressed in a stepwise approach. Prioritized may include a particular order of steps which need to be completed in a particular order. An aspect of a particular diagnosis includes one or more body systems, one or more body parts, one or more cellular processes, one or more complications and the like that may be impacted by the particular diagnosis. For instance and without limitation, a particular diagnosis such as Type 2 Diabetes Mellitus may affect body parts such as eyes, kidneys, nerves, heart, blood vessels, gums, feet, skin, and liver, where each body part may need to be addressed and treated at a particular time. In yet another non-limiting example, a particular diagnosis such as Lyme Disease may affect one or more body systems including the nervous system, the genitourinary system, the cardiovascular system, the immune system, joints, skin, endocrine system and the like. A priority treatment for Lyme Disease may include a treatment plan that focuses first on eradicating bacteria, then supporting the immune system, then tissue support of the joints, then fixing endocrinal imbalances such as balancing hormone levels, and finally symptomatic control. Treatment facets may be prioritized, where they may be generated in a stepwise approach that indicates which facet needs to be addressed and treated first, which facet needs to be treated second, and the like.

With continued reference to FIG. 1, treatment training set 148 may include a plurality of data entries containing comprehensive diagnoses correlated to priority treatment facets. For instance and without limitation, a treatment training set 148 may include a plurality of data entries containing comprehensive diagnoses that include polycystic ovarian syndrome (PCOS) correlated to priority treatment that includes a treatment plan consisting of first addressing dietary issues, second improving intestinal health, third addressing spiritual aspects of health, fourth addressing activity and fitness regimens, and fifth addressing nutraceuticals and supplementation. In yet another non-limiting example, treatment training set 148 may include a plurality of data entries containing comprehensive diagnoses that include hypothyroidism correlated to priority treatment that includes a treatment plan consisting of first detecting and correcting nutrient deficiencies, second decreasing stress through meditative techniques, support groups or psychotherapy, third improving diet by initiating an anti-inflammatory diet low in carbohydrates, fourth initiating an exercise routine, fifth utilizing chelating therapy to remove heavy metals, sixth eliminating offending medications, and seventh detoxifying any and all offending toxins inside of the body.

With continued reference to FIG. 1, treatment training set 148 may be stored within a training set database 152. Training set database 152 may include any data structure suitable for use as biological marker database 124 as described above in more detail. Priority treatment module 140 selects a treatment training set 148 as a function of a biological marker classification label 136. In an embodiment, treatment training set 148 contained within training set database 152 may be organized by diagnosis and/or biological marker classification label 136. Treatment training set 148 may contain classifier labels that may indicate particular diagnoses and/or biological marker 120 contained within a particular treatment training set 148. A "classifier label" as used in this disclosure, includes any category for data including a predication generated from a classification algorithm. Classification algorithms may include for example, logistic regression, least squares support vector machines, quadratic classifiers, kernel estimation, k-nearest neighbor, decision trees, random forests, neural networks, and/or learning vector quantization. A processor may select a treatment training set 148 containing a classifier label that matches a biological marker classification label 136. For instance and without limitation, a processor may match a treatment training set 148 containing an alert classifier label to a biological marker classification label 136 that contains an alert label. In yet another non-limiting example, a processor may match a treatment training set 148 containing a non-alert classifier label to a biological marker classification label 136 that contains a non-alert classifier label.

With continued reference to FIG. 1, priority treatment module 140 may select a treatment training set 148 by classifying user comprehensive diagnoses 144 to generate comprehensive diagnosis classification labels. Priority treatment module 140 may receive diagnostic training data, where diagnostic training data contains a plurality of data entries containing urgent and non-urgent labels. Diagnostic training data may include any of the training data as described above. An "urgent" classification label as used in this disclosure, indicates a diagnosis that requires immediate medical attention. Immediate medical attention may include for example, medical attention that is warranted within the immediate 1-2 weeks. For instance and without limitation, a diagnosis such as chest pains due to myocardial infarction, slurred speech, head injury, concussion, broken bones, influenza, seizures, serious burns, poisonings, deep gunshot wounds and the like may be diagnoses that require urgent medical attention. A "non-urgent" classification label as used in this disclosure, indicates a diagnosis that does not require immediate medical attention and can either be treated at a later point in time or may not require medical attention at all and rather may be treated by a user at home using self-care techniques. For instance and without limitation, a diagnosis such as hammertoe, pulled muscle, sprained finger, Alzheimer's disease, persistent cough, rhinovirus, minor laceration, ocular pruritus, skin rash, and the like. Priority treatment module 140 generates a classification algorithm utilizing diagnostic training data. Classification algorithm may include any classification algorithm including for example, logistic regression, fisher's linear discriminant, least squares support vector machines, quadratic classifiers, k-nearest neighbor, support vector machines, decision trees, boosted trees, random forest, neural networks, learning vector quantization, and/or any classification algorithm as described in this disclosure. Classification algorithm utilizes a plurality of user comprehensive diagnoses 144 as inputs and outputs a comprehensive diagnosis classification label for each of the plurality of user comprehensive diagnoses 144. For instance and without limitation, a first user diagnosis such as tension headache may contain a non-urgent classification label while a second user diagnosis such as myocardial infarction may include an urgent classification label. Priority treatment module 140 may select a treatment training set 148 as a function of a comprehensive diagnosis classification label for each of the plurality of user comprehensive diagnoses 144. For example, priority treatment module 140 may select a treatment training set 148 by matching a comprehensive diagnosis classification label to a classification label contained within training set database 152. In an embodiment, priority treatment module 140 may select a treatment training set 148 by matching a comprehensive diagnosis to a comprehensive diagnosis contained within a particular treatment training set 148. For instance and without limitation, a comprehensive diagnosis generated by a comprehensive advisor may include a diagnosis of Parkinson's disease. In such an instance, priority treatment module 140 may select a treatment training set 148 containing one or more data entries containing a comprehensive diagnosis of Parkinson's disease correlated to priority treatment. In yet another non-limiting example, a comprehensive diagnosis generated by a comprehensive advisor may include a diagnosis of herpes zoster, whereby priority treatment module 140 may select a treatment training set 148 containing one or more data entries containing a comprehensive diagnosis of herpes zoster correlated to priority treatment.

With continued reference to FIG. 1, priority treatment module 140 is configured to generate using a supervised machine-learning algorithm a treatment model 156 that outputs an ordered priority treatment list for each of the plurality of comprehensive diagnoses utilizing the selected treatment training set. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of comprehensive diagnoses as inputs, priority treatments as outputs, and a scoring function representing a desired form of relationship to be detected between elements of comprehensive diagnoses and priority treatments; scoring function may, for instance, seek to maximize the probability that a given element of a comprehensive diagnosis is associated with a given priority treatment and/or combination of comprehensive diagnoses to minimize the probability that a given element of a comprehensive diagnosis and/or combination of elements comprehensive diagnoses are not associated with a given priority treatment and/or combination of priority treatments. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine-learning algorithms that may be used to determine relation between comprehensive diagnoses and priority treatments. In an embodiment, one or more supervised machine-learning algorithms may be restricted to a particular domain for instance, a supervised machine-learning process may be performed with respect to a given set of parameters and/or categories of parameters that have been suspected to be related to a given set of comprehensive diagnoses, and/or are specified as linked to a medical specialty and/or field of medicine covering a particular body system or medical specialty. As a non-limiting example, a particular set of diagnoses that indicate emergency medical conditions may be typically associated with a known urgency to seek medical attention and be treated, and a supervised machine-learning process may be performed to relate those comprehensive diagnoses to priority treatments; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate priority treatments. Additional supervised learning processes may be performed without domain restrictions to detect, for instance, previously unknown and/or unsuspected relationships between comprehensive diagnoses and priority treatments.

With continued reference to FIG. 1, treatment model 156 is a machine-learning process that may include linear or polynomial regression algorithms, may include calculating one or more equations, may include a set of instructions to generate outputs based on inputs which may be derived using any machine-learning algorithm and the like.

With continued reference to FIG. 1, priority treatment module 140 evaluates priority treatment facets for each of the plurality of comprehensive diagnoses. Evaluating priority treatment may include evaluating each of the stepwise approaches contained within a treatment plan to find overlap and eliminate competing facets. For instance and without limitation, evaluating priority treatment facets may include evaluating a stepwise approach contained within a priority treatment for a first comprehensive diagnosis such as tension headache which includes a first facet approach to correct nutritional deficiencies, a second facet approach to institute a meditation practice, and a third facet approach to initiate an anti-inflammatory diet. Priority treatment module 140 may evaluate priority treatment facets for a first comprehensive diagnosis in conjunction with a second comprehensive diagnosis such as persistent depressive disorder which includes a first facet approach to initiate an anti-inflammatory diet, a second facet approach which includes initiating an exercise regimen, a third facet approach which includes addressing gastrointestinal disbalances, and a fourth facet approach which includes initiating an anti-depressant medication. Evaluating may include comparing priority treatments to identify shared facet approaches. For instance in the above example, first comprehensive diagnosis includes a facet approach to initiate an anti-inflammatory diet and second comprehensive diagnosis includes a facet approach to initiate an anti-inflammatory diet. In yet another non-limiting example, evaluating may include identifying facets that need to be completed first before other facets can be addressed. For instance and without limitation, in the above example priority treatment module 140 may identify that correcting nutritional deficiencies needs to be performed before gastrointestinal disbalances can be addressed.

With continued reference to FIG. 1, evaluating priority treatment includes retrieving an element of user symptom data from user database. An "element of user symptom data" as used in this disclosure, includes an element of data describing one or more symptoms that a user may be experiencing currently, one or more symptoms that a user may have experienced in the past, and/or one or more symptoms that a user may be experiencing recurrently or intermittently. In an embodiment, an element of user symptom data may be received from a user client device 160. User client device 160 may include without limitation, a display in communication with a processor, where a display may include any display as described herein. User client device 160 may include an additional computing device, such as a mobile device, laptop, desktop computer and the like. With continued reference to FIG. 1, priority treatment module 140 correlates an element of user symptom data to a comprehensive diagnosis. Correlating, as used herein, may include any relation established therein linking an element of user symptom data to a comprehensive diagnosis. Correlation may include a relation established where a particular element of user symptom data is attributed to and/or caused by a comprehensive diagnosis. For instance and without limitation, an element of user symptom data such as a runny nose may be correlated to a comprehensive diagnosis such as rhinovirus. In yet another non-limiting example, an element of user symptom data such as uncontrollable jerking movements of the arms and legs may be correlated to a comprehensive diagnosis such as epilepsy. In an embodiment, priority treatment module 140 may receive a plurality of comprehensive diagnoses and correlate a plurality of elements of user symptom data to one or more diagnoses. For instance and without limitation, priority treatment module 140 may receive a plurality of comprehensive diagnoses that include hypertension, pulmonary edema, schizophrenia, and heavy metal toxicity in addition to a plurality of elements of user symptom data that include throbbing headache, fatigue, and nighttime wakening. In such an instance, priority treatment module 140 may correlate throbbing headache to hypertension, fatigue to heavy metal toxicity, and nighttime wakening to schizophrenia. In an embodiment, one or more elements of user symptom data may be correlated to one or more comprehensive diagnoses. In an embodiment, one or more comprehensive diagnoses may be correlated to one or more elements of user symptom data. Priority treatment module 140 may correlate elements of user symptom data to one or more diagnoses using learned associations. In an embodiment, priority treatment module 140 may receive correlation training data that may include a plurality of data entries containing an element of symptom data correlated to a comprehensive diagnosis. Correlation training data may include any training data as described herein. For instance and without limitation, correlation training data may include a plurality of data entries containing symptom data such as slurred speech to a comprehensive diagnosis such as stroke. Priority treatment module 140 may correlate elements of user symptom data to one or more diagnoses by consulting an expert database 164 that may contain expert input regarding one or more elements of symptom data correlated to one or more comprehensive diagnoses. Expert database 164 may include any data structure suitable for use as biological marker database 124 as described above. Expert database 164 may include one or more data entries generated by top experts in a particular field of knowledge, expert scientific articles, journals, literature, and the like as described in more detail below. User symptom data correlated to one or more comprehensive diagnoses may be utilized to generate a treatment instruction set 172 as described below in more detail. Expert database 164 may receive inputs from advisor client device 168. Advisor client device 168 may include any device suitable for use as user client device 160 as described above.

With continued reference to FIG. 1, priority treatment module 140 is configured to generate a treatment instruction set 172. A "treatment instruction set" as used in this disclosure, includes a stepwise recommended approach for the treatment by a comprehensive advisor of one or more comprehensive diagnoses. Treatment instruction set may include a series of one or more textual statements. Treatment instruction set may be altered and/or transformed by priority treatment module 140 to be able to be displayed on a graphical user interface. For example, treatment instruction set containing a series of one or more textual statements may be transformed by priority treatment module 140 to be displayed on a graphical user interface to be displayed by converting one or more entries into characters or numerical outputs readable by a processor 104. A stepwise recommended approach includes a series of one or more facets of each comprehensive diagnosis that must be addressed and treated first before another facet can be addressed. A stepwise recommended approach includes facets from one or more comprehensive diagnoses. In an embodiment, priority treatment module 140 may evaluate one or more facets from one or more comprehensive treatments to generate a treatment instruction set 172 that includes a stepwise recommended approach for all of the plurality of user comprehensive diagnoses 144 put together. Generating a treatment instruction set 172 may include receiving input from one or more comprehensive advisors. Priority treatment module 140 may receive a comprehensive input descriptor generated by a comprehensive advisor on a graphical user interface 116 located on a processor. A "comprehensive input descriptor" as used in this disclosure, includes a summary detailing one or more encounters between a comprehensive advisor and a user. An "encounter" as used in this disclosure, includes one or more consultation events between a comprehensive advisor and a user. A consultation event may include an in person face to face meeting, a telephonic meeting, a telegraphic meeting such as a meeting conducted over a network interface, an email communication, a communication processed over a messaging service and the like. A comprehensive input descriptor may contain one or more advisory interaction summaries containing information detailing what a comprehensive advisor's own treatment plan is for a user or what the comprehensive advisor wishes to focus on next. An advisory interaction summary may contain a description of one or more comprehensive diagnoses pertaining to a user such as how advanced a particular comprehensive diagnosis is or what stage a particular comprehensive diagnosis is currently at. An advisory interaction summary may contain a description of one or more findings a comprehensive advisor discovered during a physical examination of a user. An advisory interaction summary may contain a description of one or more symptoms a user may have discussed with comprehensive advisor during an encounter. Comprehensive input descriptor may be utilized to generate an ordered treatment plan. In an embodiment, an advisory interaction summary that contains a description of one or more symptoms that a user is currently experiencing may cause one or more prioritized treatment facets to be placed ahead of another treatment facet or for one treatment facet to be placed behind another treatment facet when generating ordered treatment plan. For instance and without limitation, an advisory interaction summary that contains a description of a symptom a user is experiencing such as toe pain as a result of a comprehensive diagnosis of gout, may be utilized to place a first treatment facet that contains a diet low in uric acid ahead of a second treatment facet that contains a recommendation to initiate heavy metal detoxification. In yet another non-limiting example, an advisory interaction summary that contains a description from a physical examination of a user may contain a description of a current finding on a user's body that contains a description of multiple petechiae on the skin. In such an instance, generating an ordered treatment plan may include placing a first treatment facet that contains initiating an anti-inflammatory diet behind a second treatment facet that contains directions to apply hydrocortisone cream to the body area affected by petechiae, when generating an ordered treatment plan.

With continued reference to FIG. 1, data describing an advisory interaction summary and/or data describing one or more expert inputs may alternatively or additionally be extracting from one or more documents or entries utilizing a language processing module 176. Language processing module 176 may include any hardware and/or software module. Language processing module 176 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams" where all sequences of n consecutive characters are considered. Any or all possible sequences of tokens or words may be stored as "chains", for example for use as a Markov chain or Hidden Markov Model.

Still referring to FIG. 1, language processing module 176 may compare extracted words to categories of advisory inputs, such data for comparison may be entered on processor 104 as described above using expert data inputs or the like. In an embodiment, one or more categories may be enumerated, to find total count of mentions in such documents. Alternatively or additionally, language processing module 176 may operate to produce a language processing model. Language processing model may include a program automatically generated by processor 104 and/or language processing module 176 to produce associations between one or more words extracted from at least a document and detect associations, including without limitation mathematical associations, between such words, and/or associations of extracted words with categories of dietary data, relationships of such categories to alimentary labels, and/or categories of alimentary labels. Associations between language elements, where language elements include for purposes herein extracted words, categories of advisory interactions, relationships of such categories to users, and/or categories of expert inputs may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of advisory interaction summary, a given relationship of such categories to users, and/or a given category of expert inputs. As a further example, statistical correlations and/or mathematical associations may include probabilistic formulas or relationships indicating a positive and/or negative association between at least an extracted word and/or a given category of advisory interaction summaries, a given relationship of such categories to users, and/or a given category of expert inputs; positive or negative indication may include an indication that a given document is or is not indicating a category of an advisory interaction summary, relationship of such category to a user, and/or category of expert inputs is or is not significant. For instance, and without limitation, a negative indication may be determined from a phrase such as "joint pain was not found to be associated with hypothyroidism" whereas a positive indication may be determined from a phrase such as "joint pain was found to be associated with osteoarthritis" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at processor 104, or the like.

Still referring to FIG. 1, language processing module 176 and/or processor 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word and a category of an advisory interaction summary, a given relationship of such categories to users, and/or a given category of expert inputs. There may be a finite number of category of dietary data, a given relationship of such categories to advisory interaction summaries, and/or a given category of expert input to which an extracted word may pertain; an MINI inference algorithm, such as the forward-backward algorithm or the Viterbi algorithm, may be used to estimate the most likely discrete state given a word or sequence of words. Language processing module 176 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 176 may use a corpus of documents to generate associations between language elements in a language processing module 176, and processor 104 may then use such associations to analyze words extracted from one or more documents and determine that the one or more documents indicate significance of a category of advisory interaction summary, a given relationship of such categories to users, and/or a given category of expert inputs. In an embodiment, processor 104 may perform this analysis using a selected set of significant documents, such as documents identified by one or more experts as representing good science, good clinical analysis, or the like; experts may identify or enter such documents via graphical user interface 116 as described below in more detail or may communicate identities of significant documents according to any other suitable method of electronic communication, or by providing such identity to other persons who may enter such identifications into processor 104. Documents may be entered into processor 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, processor 104 may automatically obtain the document using such an identifier, for instance by submitting a request to a database or compendium of documents such as JSTOR as provided by Ithaka Harbors, Inc. of New York.

With continued reference to FIG. 1, generating treatment instruction set 172 includes retrieving a user diagnostic factor input from user database where the user diagnostic factor input includes a long-term target indicator and a short-term target indicator. A "user diagnostic factor input" as used in this disclosure, includes any data describing a user's health goals as they relate to a particular comprehensive diagnosis. "User health goals" as used in this disclosure, includes any user desire or outcome a user seeks to achieve in reference to a particular comprehensive diagnosis. A user diagnostic factor input includes a long term target indicator. A "long term target indicator" as used in this disclosure, includes any long term goal that a user seeks to achieve. A long term goal may include an outcome that a user doesn't seek to remedy immediately but rather seeks to remedy or achieve it at a later point in the future. For instance and without limitation, a long term target indicator may include a desire to reverse a chronic illness or eliminate the need to manage a comprehensive diagnosis with medication. A user diagnostic factor input includes a short term target indicator. A "short term target indicator" as used in this disclosure, includes any short term goal that a user seeks to achieve. A short term goal may include an outcome that a user seeks to remedy or achieve in the immediate future. A short term target indicator may include a short term goal that a user seeks to achieve such as to reduce the number of episodes of a particular disease or a desire to rely on less medication to manage a particular comprehensive diagnosis.

With continued reference to FIG. 1, priority treatment module 140 is configured to generate a loss function utilizing a user diagnostic factor input and minimize the loss function. Mathematical expression may represent a loss function, where a "loss function" is an expression an output of which an optimization algorithm minimizes to generate an optimal result. As a non-limiting example, priority treatment module 140 may calculate variables reflecting scores relating to particular user diagnostic factor inputs, calculate an output of mathematical expression using the factor inputs, and generate an ordered treatment plan that produces an output having the lowest size, according to a given definition of "size," of the set of outputs representing each of the plurality of ordered treatment plans; size may, for instance, included absolute value, numerical size, or the like. Selection of different loss functions may result in identification of different ordered treatment plans as generating minimal outputs; for instance, where a long-term target indicator is associated in a first loss function with a large coefficient or weight, a short-term target indicator having a small coefficient or weight for may minimize the first loss function, whereas a second loss function wherein long-term indicator has a smaller coefficient which has a larger coefficient may produce a minimal output for a different ordered treatment plan having a larger short-term indicator.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user inputs as above. User may enter a new command changing mathematical expression, and then subsequent user inputs may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Priority treatment module 140 may utilize variables to model relationships between past interactions between a user and system 100 and ordered treatment plans. In an embodiment loss function analysis may utilize variables that may impact user interactions and/or short-term target indicators and/or long-term target indicator. Loss function analysis may be user specific so as to create algorithms and outputs that are customize to variables for an individual user.

With continued reference to FIG. 1, generating an ordered treatment plan may include calculating a comprehensive diagnosis impact score where the comprehensive diagnosis impact score includes a difficulty factor multiplied by an alimentary standard factor multiplied by an implementation factor. A "comprehensive diagnosis impact score" as used in this disclosure, includes one or more attributes that may affect a diagnosis. An attribute may include any factor that may attribute to a diagnosis including how difficult it may be to seek treatment, how much money a particular treatment may cost, accessibility to receive treatment, travel time to treatment and the like. Factors may be received from user inputs, from user-client device and/or may be stored in user database. A "difficulty factor" as used in this disclosure, indicates how difficult a particular treatment facet is to implement. Difficulty factor may be rated on a numerical score ranging from 0 to 100 where 0 may indicate a particular treatment facet that is not difficult to implement and 100 may indicate a particular treatment facet that is very difficult to implement. For instance and without limitation, a user may rate a treatment facet such as adhering to a low sugar diet as 85, indicating a difficult treatment to implement while the user may rate a treatment facet such as consuming a medication once per day as 10, indicating a treatment that is not difficult to implement. An "alimentary standard factor" as used in this disclosure, indicates how expensive a particular treatment facet is to implement. Alimentary standard factors may be rated on a numerical score ranging from 0 to 100 where 0 may indicate an inexpensive treatment facet and 100 may indicate a particular treatment facet that is very expensive to implement. Alimentary standard factors may be calculated based on expert input. For instance and without limitation, a treatment facet such as a mammogram may contain an alimentary standard factor as 72 while a treatment facet such as practicing a meditation sequence may contain an alimentary standard factor as 15. An "implementation factor" as used in this disclosure, indicates how difficult a particular treatment facet is to implement into one's daily life treatment. Implementation factor may be based upon user inputs received from user database and/or user client device 160 and/or based on expert input. Implementation factor may be rated on a numerical score ranging from 0 to 100 where 0 may indicate a particular treatment facet that is not difficult to implement while a score of 100 may indicate a particular treatment facet that is difficult to implement. For instance and without limitation, a treatment facet such as implementing a fitness routine may contain an implementation factor score of 87 while a treatment facet such as taking a fish oil capsule once per day may contain an implementation factor score of 12.

Figure 2:
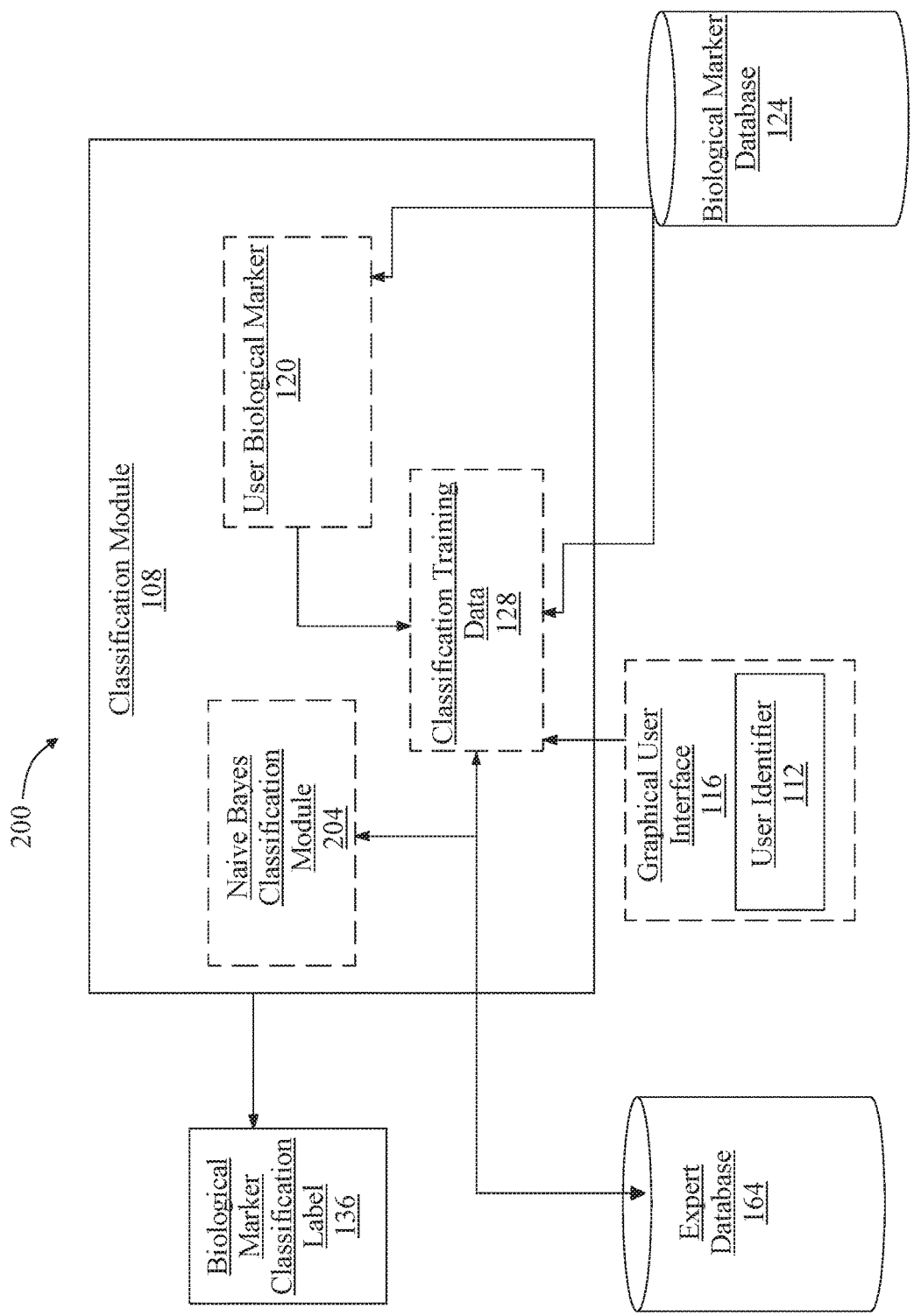
FIG. 2 is a block diagram illustrating an exemplary embodiment of a classification module.

Referring now to FIG. 2, an exemplary embodiment 200 of classification module 108 is illustrated. Classification module 108 may be implemented as any hardware and/or software module. Classification module 108 receives a user identifier 112 entered by a comprehensive advisor located on graphical user interface 116. User identifier 112 may include any of the user identifier 112 as described above in reference to FIG. 1. For instance and without limitation, user identifier 112 may include a user's name and address, a particular medical record for a user, or a public private cryptographic key pair. In an embodiment, user identifier 112 may be selected from user database upon entry of information pertaining to a particular user by comprehensive advisor on graphical user interface 116. For instance and without limitation, comprehensive advisor may select a particular user from a list displayed upon graphical user interface 116 of a plurality of users, upon selecting a particular user from the list, a user identifier 112 may be retrieved from user database. In yet another non-limiting example, a user identifier 112 entered by a comprehensive advisor on graphical user interface 116 may be utilized to confirm information pertaining to a user that may be stored within user database. For example, a comprehensive advisor may enter a user's name and date of birth on graphical user interface 116, which may prompt processor 104 and/or classification module 108 to retrieve stored information about a user within user database such as medical history, demographics, emergency contact information and the like. Stored information pertaining to a user within user database may be displayed upon graphical user interface 116 for a comprehensive advisor to confirm or edit such as when a comprehensive advisor may be having a face to face appointment with a user and seeks to update information.

With continued reference to FIG. 1, classification module 108 retrieves a user biological marker 120 from biological marker database 124. User biological marker 120 includes any of the user biological marker 120 as described above in reference to FIG. 1. For instance and without limitation, a user biological marker 120 may include a urinalysis analyzed for heavy metals including lead, iron, cadmium, mercury, aluminum, arsenic, cesium, nickel, palladium, thallium, tungsten, and uranium. In yet another non-limiting example, a user biological marker 120 may include a salivary hormone panel analyzed for one or more hormone levels including cortisol, testosterone, DHEA, estradiol, estriol, estrone, and progesterone. Biological marker 120 stored within biological marker database 124 may have been previously collected and analyzed. For instance and without limitation, biological marker database 124 may contain entries containing all biological marker 120 extracted and analyzed over the course of a user's lifestyle. Comprehensive advisor input generated through graphical user interface 116 may prompt classification module 108 to retrieve a particular biological marker 120 collected and analyzed on a particular day and/or time. In an embodiment, biological marker database 124 may contain a user identifier 112 that may be confirmed before retrieving a user biological marker 120. For instance and without limitation, a user identifier 112 such as a user's name and date of birth may be compared and matched to a user's name and date of birth associated with a particular biological marker 120.

With continued reference to FIG. 2, classification module 108 receives classification training data 128. Classification training data 128 may include any of the classification training data 128 as described above in reference to FIG. 1. Classification training data 128 includes a plurality of data entries containing biological marker 120 data containing alert and non-alert classification labels. For instance and without limitation, classification training data 128 may include a plurality of data entries containing one or more biological marker 120 data entries containing alert and non-alert classification labels. For example, a particular set of classification training data 128 may include a plurality of biological marker 120 containing varied biological marker 120 including methane breath levels, cerebrospinal neutrophil levels, salivary testosterone levels, and mercury hair levels containing alert and non-alert classification labels. In yet another non-limiting example, a particular set of classification training data 128 may include a plurality of data entries containing the same biological marker 120 containing alert and non-alert classification labels. For example, classification training data 128 may include a first salivary progesterone level containing an alert label, a second salivary progesterone level containing a non-alert classification label, a third salivary progesterone level containing an alert classification label, and a fourth salivary progesterone level containing a non-alert classification label.

With continued reference to FIG. 2, classification module 108 may receive classification training data 128 from expert database 164. Expert database 164 may be implemented as any data structure suitable for use as biological marker database 124 as described above. Classification training data 128 may be generated from expert inputs stored within expert database 164. Expert input may provide advice as to what classification training data 128 sets may be best suited to be utilized for generating algorithms for particular user biological marker 120. For instance and without limitation, a particular set of classification training data 128 may contain data entries that contain a biological marker 120 that matches a user biological marker 120. For instance and without limitation, expert input contained within expert database 164 may recommend that a particular classification training set contained within expert database 164 that includes a plurality of data entries containing a biological marker 120 such as urinary bisphenol A levels may be best suited to a user biological marker 120 that contains a urinary bisphenol A level measurement. In yet another non-limiting example, expert input contained within expert database 164 may recommend that a particular classification training set contained within expert database 164 that includes a plurality of data entries containing a biological marker 120 such as salivary progesterone may not be best suited to a user biological marker 120 that contains a plasma progesterone level.

With continued reference to FIG. 2, classification module 108 may include naïve Bayes classification module 204. Naïve Bayes classification module 204 may be implemented as any hardware and/or software module. Naïve Bayes classification module 204 generates a naïve Bayes classification algorithm utilizing classification training data 128. A naïve Bayes classification algorithm utilizes a user biological marker 120 as an input and outputs a biological marker classification label 136. Naïve Bayes classification module 204 generates a naïve Bayes classification algorithm utilizing any of the methods as described above in reference to FIG. 2. Naïve Bayes classification module 204 generates a naïve Bayes classification algorithm based on an assumption that each data entries contained within classification training set makes an independent and equal contribution to an outcome. Naïve Bayes classification module 204 generates naïve Bayes algorithm based on principles of probabilistic classifier. Naïve Bayes algorithm includes any mathematical formulas, calculations, and the like utilized to output a biological marker classification label 136. Naïve Bayes algorithm seeks to assign classification labels to problem instances which may be represented as vectors of feature values, and where classification labels may be drawn to a finite set. Naïve Bayes algorithm includes a series of calculations that assume the value of a particular data entry is independent of the value of any other feature, given a class variable. Naïve Bayes classification module 204 may be configured to calculate one or more variations of naïve Bayes algorithm including for example gaussian naïve Bayes, multinomial naïve Bayes, Bernoulli naïve Bayes, and/or semi-supervised parameter estimation. In an embodiment, naïve Bayes classification module 204 may select a particular naïve Bayes algorithm and/or series of calculations based on input from expert database 164.

With continued reference to FIG. 2, naïve Bayes classification module 108 generates an output containing biological marker classification label 136. Biological marker classification label 136 may include any of the biological marker classification label 136s as described above in reference to FIG. 1. In an embodiment, biological marker classification label 136 may include a classification label containing an alert or non-alert classification label. In an embodiment, biological marker classification label 136 may include other classification labels that may be determined based on expert input and data entries contained within classification training data 128.

Figure 3:
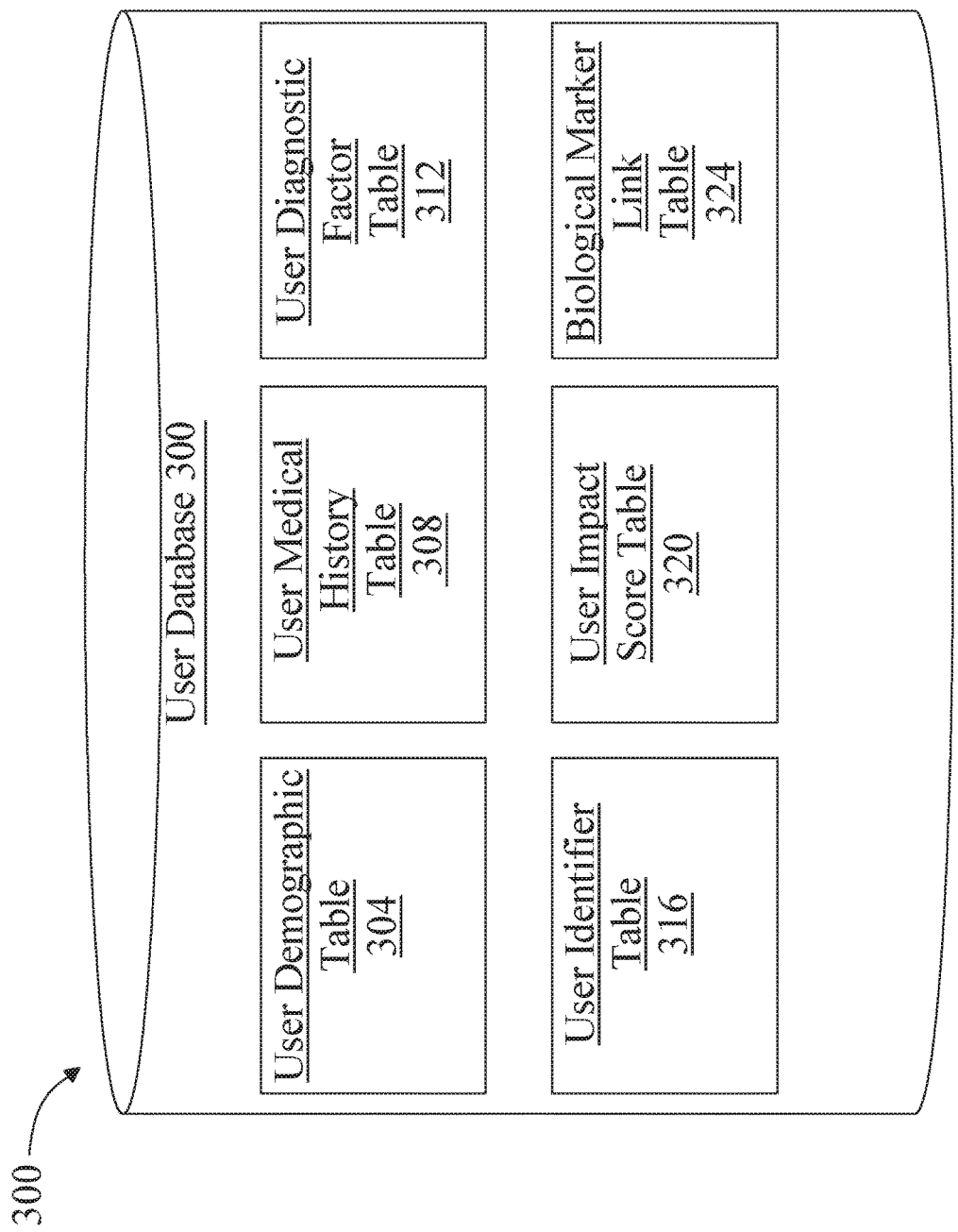
FIG. 3 is a block diagram illustrating an exemplary embodiment of a user database.

Referring now to FIG. 3, an exemplary embodiment of user database 300 is illustrated. User database 300 may be implemented as any data structure suitable for use as biological marker database 124 as described above in more detail in reference to FIG. 2. One or more tables contained within user database 300 may include user demographic table 304; user demographic table 304 may include one or more data entries relating to a user's demographics. For instance and without limitation, user demographic table 304 may include information relating to a user's full legal name, address, work address, marital status, income, occupation, and the like. One or more tables contained within user database 300 may include user medical history table 308; user medical history table 308 may include one or more data entries containing a user's medical history. For instance and without limitation, user medical history table 308 may include information describing a user's current and previous medications, allergies, surgeries, medical procedures, office visits, emergency room visits, consultations and appointments with comprehensive advisors and the like. One or more tables contained within user database 300 may include user diagnostic factor table 312; user diagnostic factor table 312 may include one or more data entries containing user diagnostic factors including long-term target indicators and short-term target indicators. For instance and without limitation, user diagnostic factor table 312 may include a current long-term target indicator entered by a user and a current short-term target indicator relating to a particular comprehensive diagnosis. One or more tables contained within user database 300 may include user identifier 112 table 316; user identifier 112 table 316 may include one or more data entries containing one or more user identifier 112. For instance and without limitation, user identifier 112 table 316 may include user identifier 112 that include a user's name, address, date of birth, public-private cryptographic key pairs, biometric authentications and the like. One or more tables contained within user database 300 may include user impact score table 320; user impact score 320 may include one or more data entries containing a user impact score. For instance and without limitation, user impact score table 320 may include a user impact score generated by a user in regards to a particular treatment facet. One or more tables contained within user database 300 may include biological marker 120 link table 324; biological marker 120 link table 324 may include one or more links of user data contained within user database 300 to information contained within biological marker database 124.

Figure 4:
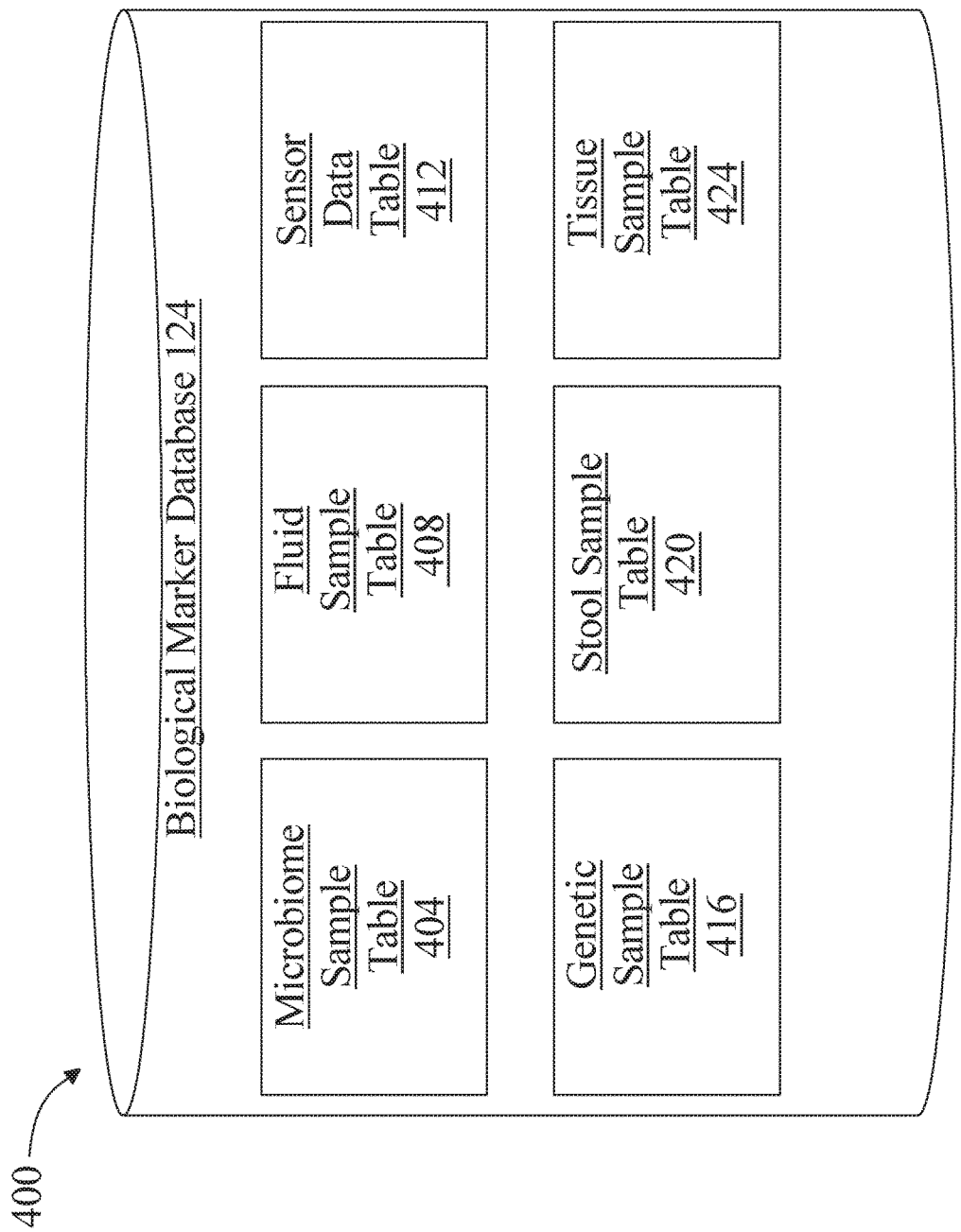
FIG. 4 is a block diagram illustrating an exemplary embodiment of a biological marker database.

Referring now to FIG. 4, an exemplary embodiment 400 of biological marker database 124 is illustrated. Biological marker database 124 may include any data structure as described above in reference to FIG. 1. Biological marker database 124 may store one or more biological marker 120. One or more tables contained within biological marker database 124 may include microbiome sample table 404; microbiome sample table 404 may store one or more biological marker 120 relating to the microbiome. For instance and without limitation, microbiome sample table 404 may include results reflecting levels of a particular bacterial strain such as quantities of *Bifidobacterium* found in a user's gastrointestinal tract. One or more tables contained within biological marker database 124 may include fluid sample table 408; fluid sample table 408 may store one or more biological marker 120 obtained from a fluid sample. For instance and without limitation, fluid sample table 408 may include one or more entries containing results from fluids such as urine, saliva, sweat, tears, blood, mucus, cerebrospinal fluid, and the like analyzed for one or more biological marker 120. One or more tables contained within biological marker database 124 may include sensor data table 412; sensor data table 412 may include one or more biological marker 120 obtained from one or more sensors. For instance and without limitation, sensor data table 412 may include sleeping patterns of a user recorded by a sensor. One or more tables contained within biological marker database 124 may include genetic sample table 416; genetic sample table 416 may include one or more biological marker 120 containing one or more genetic sequences. For instance and without limitation, genetic sample table 416 may include a user's genetic sequence for a particular gene such as a sequence illustrating a positive breast cancer one (BRACA 1) gene. One or more tables contained within biological marker database 124 may include stool sample table 420; stool sample table 420 may include one or more biological marker 120 obtained from a stool sample. For instance and without limitation, stool sample table 420 may include a user's stool sample analyzed for the presence and/or absence of one or more parasites. One or more tables contained within biological marker database 124 may include tissue sample table 424; tissue sample table 424 may include one or more biological marker 120 obtained from one or more tissue samples. For instance and without limitation, tissue sample table 424 may include a breast tissue sample analyzed for the absence and/or presence of estrogen markers. Other tables not illustrated may include but are not limited to epigenetic, gut wall, nutrients, metabolism, and user database link table.

Figure 5B:
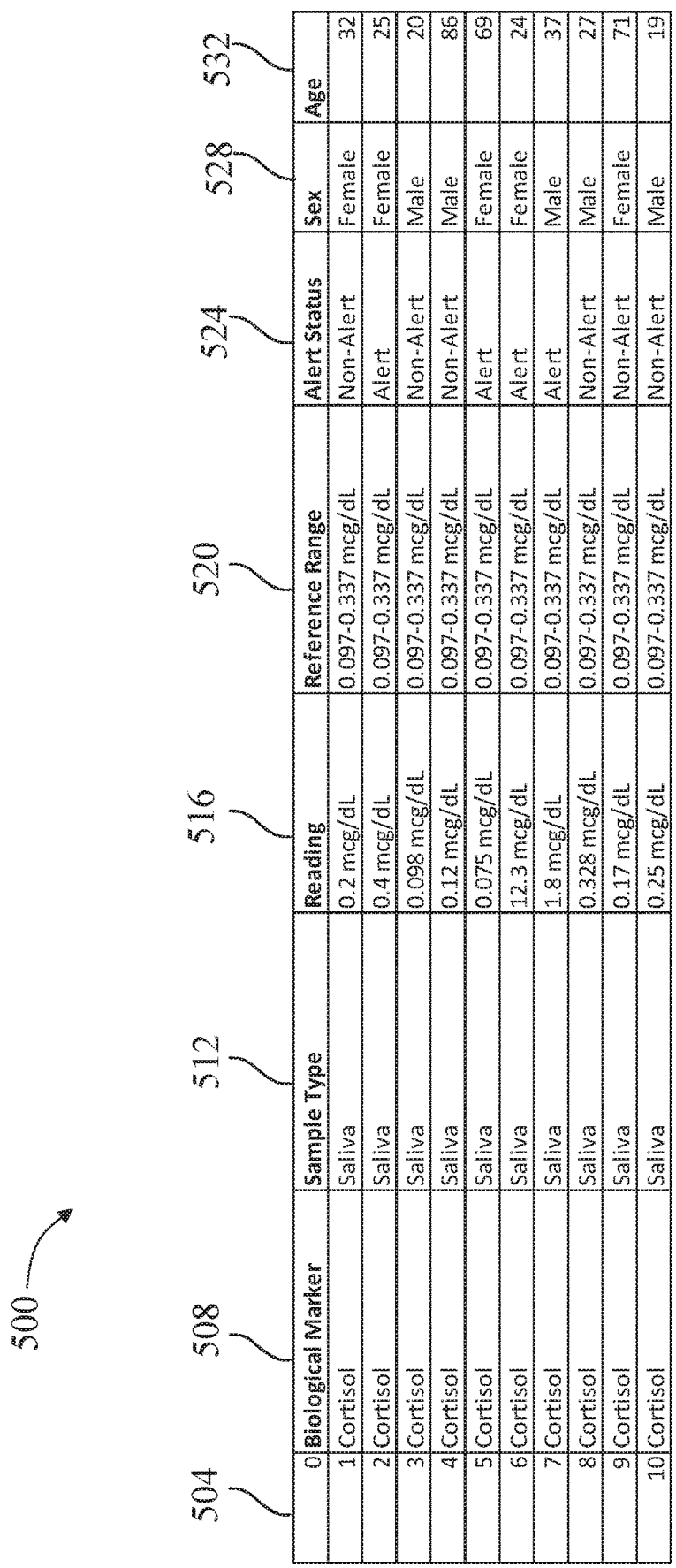

Referring now to FIGS. 5A-5B, an exemplary embodiment 500 of classification training data 128 is illustrated. Referring now to FIG. 5A, an embodiment of classification training data 128 containing a plurality of biological makers is illustrated. In an embodiment, classification training data 128 may include a plurality of data entries 504. Each data entry 504 may include a particular identified biological marker 120 508. In FIG. 5A, data entries 504 each contain varying biological marker 120. For instance and without limitation, a biological marker 120 may include cortisol, bisphenol A, pancreatic elastase, *Enterobacter cloacae*, estrone sulfate, zonulin family peptide, methane, glucose, DHEA-S, lead, and the like. Each data entry 504 may indicate a particular sample type 512 of each biological marker 120 508 identified. For instance and without limitation, a biological marker 120 508 such as cortisol may be obtained and analyzed from saliva, blood, urine, and tissue samples. Sample type 512 indicates which particular sample from a human body was extracted. Each data entry 504 may include a particular reading 516 or measurement obtained from a particular sample. Each data entry 504 may include a reference range 520 for each particular biological marker 120 508 which may be adjusted based on what particular sample type 512 was extracted. For example, a reference range 520 for plasma progesterone levels may be different than a reference range 520 for salivary progesterone levels. Each data entry 504 contains an alert status 524 which includes a classification label containing an alert or non-alert classification label. Each data entry 504 contains a gender identifier 528 which indicates what sex the data entry 504 was received from. Each data entry 504 contains an age identifier 532 which indicates what age the data entry 504 was received from.

Referring now to FIG. 5B, an embodiment of classification training data 128 containing one type of biological marker 120 504 is illustrated. In an embodiment, classification training data 128 may include a plurality of data entries 504. Each data entry 504 may include the same identified biological marker 120 508. In FIG. 5B, data entries 504 each contain the same biological marker 120 508, cortisol. Each data entry 504 may indicate a particular sample type 512 of each biological marker 120 508 identified. In an embodiment, sample type 512 may be the same, such as in FIG. 5B where the sample type is exclusively saliva. Sample type 512 indicates which particular sample from a human body was extracted. Each data entry 504 may include a particular reading 516 or measurement obtained from a particular sample. Each data entry 504 may include a reference range 520 for each particular biological marker 120 508 which may be adjusted based on what particular sample type 512 was extracted. Each data entry 504 contains an alert status 524 which includes a classification label containing an alert or non-alert classification label. Each data entry 504 contains a gender identifier 528 which indicates what sex the data entry 504 was received from. Each data entry 504 contains an age identifier 532 which indicates what age the data entry 504 was received from. In an embodiment, various combinations of biological marker 120, sample types, sex, age, and other variables containing within classification training set are possible.

With continued reference to FIGS. 5A-5B, classification training data 128 may be stored in any suitable data and/or data type. For instance and without limitation, clustering dataset may include textual data such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 5, classification training data 128 may be stored as image data, such as for example an image of a particular food substance such as a photograph of a pear or an image of a steak. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

Figure 6:
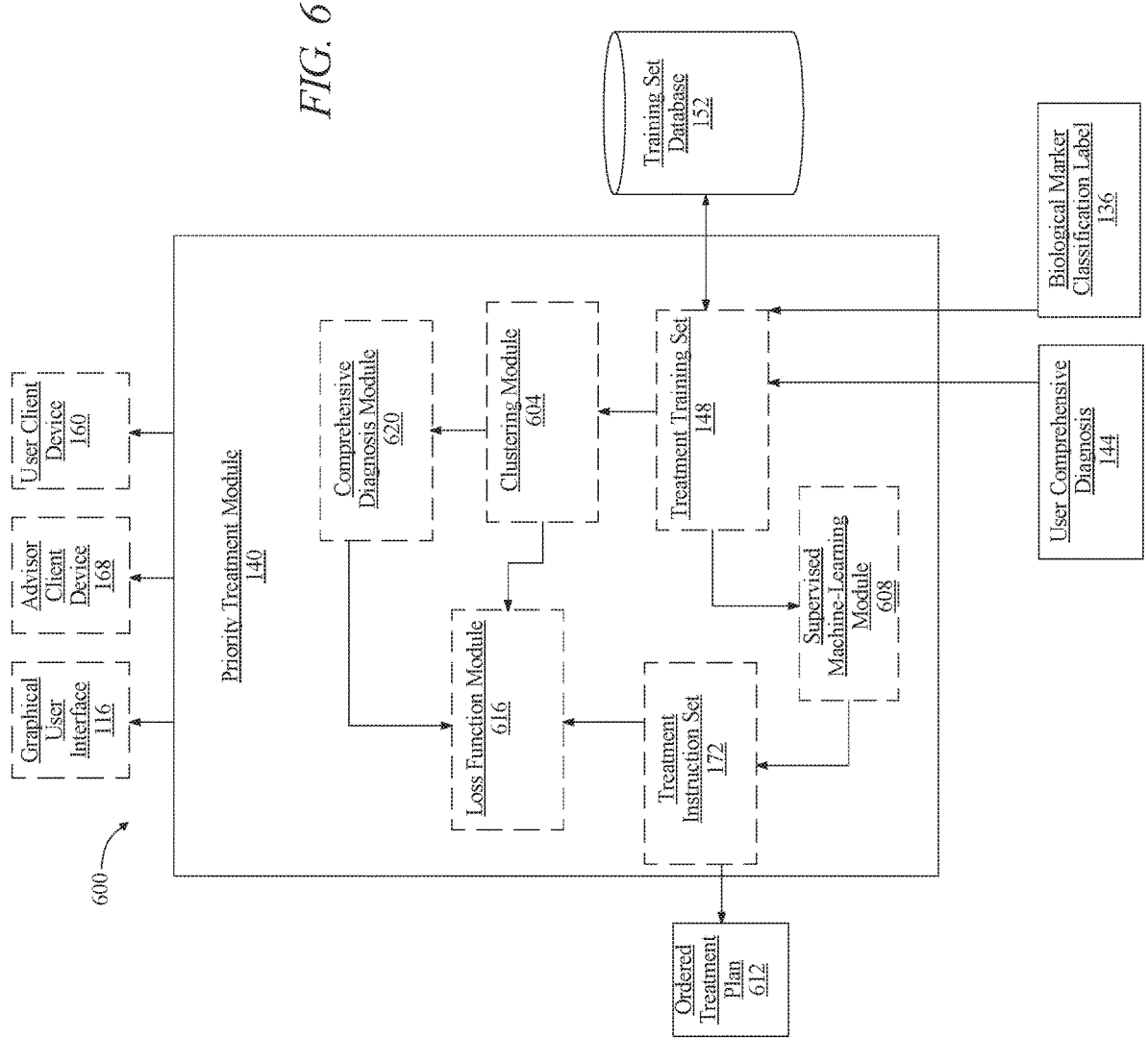
FIG. 6 is a block diagram illustrating an exemplary embodiment of a priority treatment module.

Referring now to FIG. 6, an exemplary embodiment 600 of priority treatment module 140 is illustrated. Priority treatment module 140 may include any hardware and/or software module. Priority treatment module 140 is configured to receive a biological marker classification label 136 from classification module 108. Priority treatment module 140 receives a biological marker classification label 136 from classification module 108 utilizing any network topography as described herein. Priority treatment module 140 receives a plurality of user comprehensive diagnoses 144. User comprehensive diagnoses 144 include any of the user comprehensive diagnoses 144 as described above in reference to FIG. 1. Plurality of user comprehensive diagnoses 144 relate to the same user. For instance and without limitation, a plurality of user comprehensive diagnoses 144 may include rheumatoid arthritis, back strain, hearing loss, and Alzheimer's disease. In yet another non-limiting example, a plurality of user comprehensive diagnoses 144 may include estrogen dominance, generalized anxiety disorder, and leaky gut. User comprehensive diagnoses 144 may be entered by comprehensive advisor through a graphical user interface 116. In yet another non-limiting example, comprehensive advisor may select one or more comprehensive diagnoses that may be stored within user database.

With continued reference to FIG. 6, priority treatment module 140 selects a treatment training set 148. Treatment training set 148 may be stored within training set database 152. Training set database 152 may be implemented as any data structure suitable for use as biological marker database 124 as described above. Treatment training set 148 contains a plurality of data entries containing comprehensive diagnoses correlated to one or more prioritized treatment facets. Prioritized treatment facets include any of the prioritized treatment facets as described above in reference to FIG. 1. Prioritized treatment facet includes an identification of what aspect of a comprehensive diagnosis needs to be addressed and treated in a sequential manner. For instance and without limitation, prioritized treatment facet for a comprehensive diagnosis such as small intestinal bacterial overgrowth (SIBO) may include a first facet that includes eradicating overgrowth of bacteria in small intestine, a second facet that includes addressing nutritional deficiencies, a third facet that includes initiating a low-FODMAP diet, and a fourth facet that includes repopulating beneficial bacteria.

With continued reference to FIG. 6, priority treatment module 140 selects a treatment training set 148 as a function of biological marker classification label 136. Priority treatment module 140 may select a treatment training set 148 that contains a classifier label that matches a biological marker classification label 136. Treatment training set 148 contained within training set database 152 may be organized according to various classifier labels. Treatment training set 148 may be organized within training set database 152 by classifier labels such as by alert or non-alert classifier or by type of comprehensive diagnosis training data contained within a particular treatment training set 148. Matching may include determining that a classifier label contained within training set database 152 is the same as a biological marker classification label 136. For example, a biological marker classification label 136 that contains an alert classifier label may be matched to a treatment training set 148 that contains an alert classifier label. In yet another non-limiting example, a biological marker classification label 136 that contains a classifier label by comprehensive diagnosis that contains a comprehensive diagnosis classifier label of ulcerative colitis may be matched to a treatment training set 148 that contains a classifier label of ulcerative colitis. In an embodiment, treatment training set 148 may contain classifier labels generated by expert input such as from information stored and contained within expert database 164.

With continued reference to FIG. 6, priority treatment module 140 may include clustering module 604, which may be implemented as any hardware and/or software module. Clustering module 604 may be configured to receive diagnostic training data where diagnostic training data contains a plurality of data entries including comprehensive diagnoses including urgent and non-urgent classification labels. For instance and without limitation, diagnostic training data may include a plurality of data entries containing gout containing an urgent classification label, tension headache containing a non-urgent classification label, arthritis containing a non-urgent classification label, and myocardial infarction containing an urgent classification label. Clustering module 604 may receiving diagnostic training data from training set database 152. Clustering module 604 may be configured to generate a classification algorithm utilizing diagnostic training data. Classification algorithm may include any classification algorithm including for example but not limited to logistic regression, naïve Bayes classifier, k-nearest neighbor, support vector machines, decision trees, boosted trees, random forest, and/or neural networks. Classification algorithm utilizes a plurality of user comprehensive diagnoses 144 as input and outputs a comprehensive diagnosis classification label for each of the plurality of user comprehensive diagnoses 144. Comprehensive diagnosis classification label may include any identifier indicating if a particular comprehensive diagnosis belongs to a particular class or not. Clustering module 604 may utilize comprehensive diagnosis classification label to select a treatment training set 148 for each of the plurality of user comprehensive diagnoses 144. In an embodiment, a particular cluster containing a comprehensive diagnosis classification label may be utilized as treatment training set 148. In an embodiment, comprehensive diagnosis classification label may be matched to a treatment training set 148 containing the same classification label. Comprehensive diagnosis classification labels may be utilized to generate a treatment instruction set 172 as described in more detail below.

With continued reference to FIG. 6, priority treatment module 140 may include supervised machine-learning module 608, which may be implemented as any hardware and/or software module. Supervised machine-learning module 608 generates using a supervised machine-learning model a treatment model 156 that outputs an ordered priority treatment list for each of the plurality of comprehensive diagnoses utilizing the selected treatment training set. Supervised machine-learning model includes any of the supervised machine-learning models as described above in reference to FIG. 1. Treatment model 156 may include any machine learning process and may include linear or polynomial regression algorithms. Treatment model 156 may include equations. Treatment model 156 may include a set of instructions utilized to generate outputs based on inputs derived using a machine-learning algorithm and the like. Ordered priority treatment list includes any of the ordered priority treatment list as described above. Ordered priority treatment list may include one or more treatment facets arranged in a sequential manner. For instance and without limitation, an ordered priority treatment list for a comprehensive diagnosis such as estrogen dominance may include a first treatment facet that includes initiating a daily sauna practice, a second treatment facet that includes initiating an exercise regimen, a third treatment facet that includes using clean beauty products, a fourth treatment facet that includes initiating an estrogen dominance diet, and a fifth treatment facet that includes initiating an estrogen blocking supplement regimen.

With continued reference to FIG. 6, priority treatment module 140 evaluates ordered priority treatment list for each of the plurality of comprehensive diagnoses generated by supervised machine-learning module. Evaluating ordered priority treatment list may include determining by priority treatment module 140 how a particular priority treatment considers a user's symptoms. Priority treatment module 140 may retrieve an element of user symptom data from user database. An element of user symptom data may include any of the elements of user symptom data as described above in reference to FIG. 1. Priority treatment module 140 may correlate an element of user symptom data to a comprehensive diagnosis. Correlation may be performed utilizing any of the methods as described above in reference to FIG. 1. Priority treatment module 140 may utilize the correlated element of user symptom data to a comprehensive diagnosis to generate an ordered treatment plan 612.

With continued reference to FIG. 6, priority treatment module 140 may include loss function module 616, which may be implemented as any hardware and/or software module. Loss function module 616 may aid in generating a treatment instruction set 172 by retrieving a user diagnostic factor input from user database. User diagnostic factor input includes any user diagnostic factor input as described above in reference to FIG. 1. User diagnostic factor input includes a long-term target indicator and a short-term target indicator. For instance and without limitation, user diagnostic factor input includes a long-term target indicator such as a desire to reverse a user's comprehensive diagnosis of Type 2 Diabetes Mellitus and a short-term target indicator such as a desire to eliminate the number of hypoglycemic episodes that a user experiences each week. Loss function module generates a loss function and minimizes the loss function utilizing the user diagnostic factor input containing a long term target indicator and a short term target indicator. Loss function may be generated utilizing any of the methods as described above in reference to FIG. 1. Loss function module generates an ordered treatment plan as a function of minimizing the loss function. For instance and without limitation, a particular short-term target indicator may be utilized to generate an ordered treatment plan 612 that contains a particular treatment facet in a particular order or in front of or behind a particular second treatment facet.

With continued reference to FIG. 6, priority treatment module 140 is configured to generate a treatment instruction set. Treatment instruction set 172 includes any of the treatment instruction sets as described above in reference to FIG. 1. Treatment instruction set 172 includes an ordered treatment plan 612. An "ordered treatment plan" as used in this disclosure, includes a stepwise treatment plan for two or more comprehensive diagnoses that contains a chronological sequence of prioritized treatment facets for the two or more comprehensive diagnoses. For instance and without limitation, a first comprehensive diagnosis such as gallstones may contain prioritized treatment facets that includes a first facet recommending an anti-inflammatory diet, a second facet recommending a gallbladder flush, and a third facet recommending a fish oil supplement. A second comprehensive diagnosis such as heart disease may include a first facet that recommends taking a red rice yeast extract supplement and a second facet that recommends an anti-inflammatory diet. In such an instance, ordered treatment plan may include a stepwise treatment plan for the gallstones and the heart disease and may contain a first facet recommending an anti-inflammatory diet, a second facet recommending a gallbladder flush, a third facet recommending taking a red rice yeast extract supplement, and a fourth facet recommending taking a fish oil supplement. Facets may be ordered within ordered treatment plan based on expert inputs and machine-learning algorithms including any of the machine-learning algorithms as descried herein. Generating an ordered treatment plan may include selecting a first treatment facet as a function of a first priority treatment, selecting a second treatment facet as a function of the first treatment facet and selecting a third treatment facet as function of the second treatment facet. Generating an ordered treatment plan may include selecting a first treatment facet as a function of a first priority treatment, selecting a second treatment facet as a function of the first priority treatment, and selecting a third treatment facet as a function of the second priority treatment. Generating an ordered treatment plan may include receiving a comprehensive input descriptor generated by a comprehensive advisor that contains an advisor interaction summary. Advisor interaction summary may include any of the advisor interaction summaries as described above in more detail in reference to FIG. 1. For instance and without limitation, advisor interaction summary may include a description of a phone call between a comprehensive advisor and a user when user complained of gastrointestinal symptoms including gas, explosive diarrhea, and fatigue. In yet another non-limiting example, comprehensive advisor input may include an advisor interaction summary that includes a description of a video chat between a comprehensive advisor and a user when user described a lack of motivation and extreme sadness. Ordered treatment plan 612 may be generated based on advisor interaction summaries such as by selecting a particular treatment facet to be at a specific point in a sequential sequence of treatment facets.

With continued reference to FIG. 6, priority treatment module 140 may include comprehensive diagnosis module 620, which may be implemented as any hardware and/or software module. Comprehensive diagnosis module 620 may calculate comprehensive diagnosis impact score which may be utilized to generate treatment instruction set. Comprehensive diagnosis impact score includes a difficulty factor multiplied by an alimentary standard factor multiplied by an implementation factor. Comprehensive diagnosis impact score may include any of the comprehensive diagnosis impact scores as described above in more detail in reference to FIG. 1. Difficult factors, alimentary standard factors, and implementation factors may be obtained from user inputs received from user database, user client device 160, as well as from advisory inputs and advisor client device 168.

Figure 7:
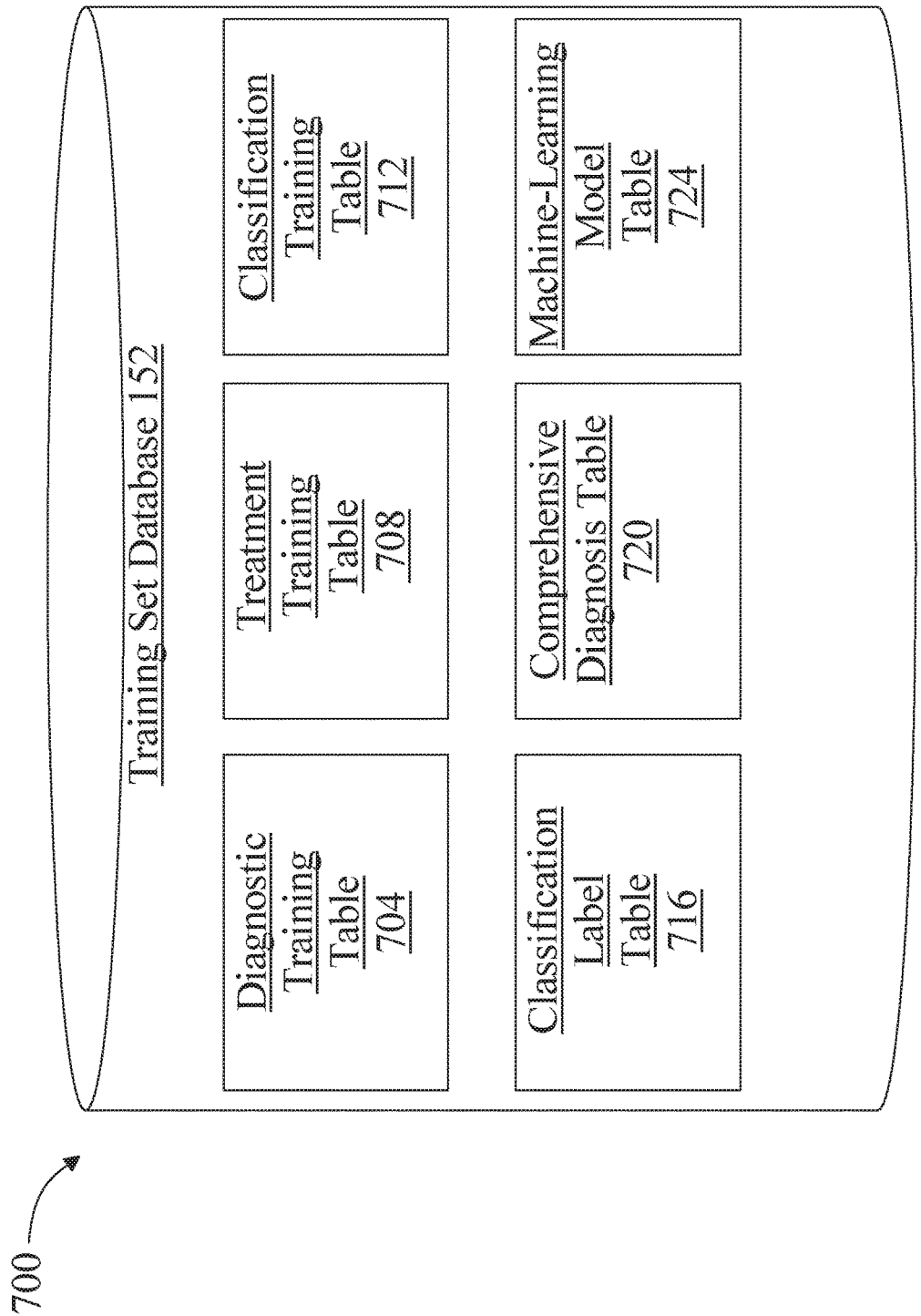
FIG. 7 is a block diagram illustrating an exemplary embodiment of a training set database.

Referring now to FIG. 7, an exemplary embodiment of training set database 152 is illustrated. Training set database 152 may be implemented as any data structure suitable for use as biological marker database 124 as described in more detail in reference to FIG. 1. One or more tables contained within training set database 152 may include diagnostic training table 704; diagnostic training table 704 may include one or more data entries containing one or more diagnostic training sets. One or more tables contained within training set database 152 may include treatment training table 708; treatment training table 708 may include one or more data entries containing one or more treatment training set 148. One or more tables contained within training set database 152 may include classification training table 712; classification training table 712 may include one or more data entries containing one or more classification training sets. One or more tables contained within training set database 152 may include classification label table 716; classification label table 716 may contain one or more training sets organized by classification labels. One or more tables contained within training set database 152 may include comprehensive diagnosis table 720; comprehensive diagnosis table 720 may include one or more training sets organized by comprehensive diagnosis. One or more tables contained within training set database 152 may include machine-learning model table 724; machine-learning model table 724 may include one or more machine-learning models that may have been previously calculated and ready to be utilized.

Figure 8:
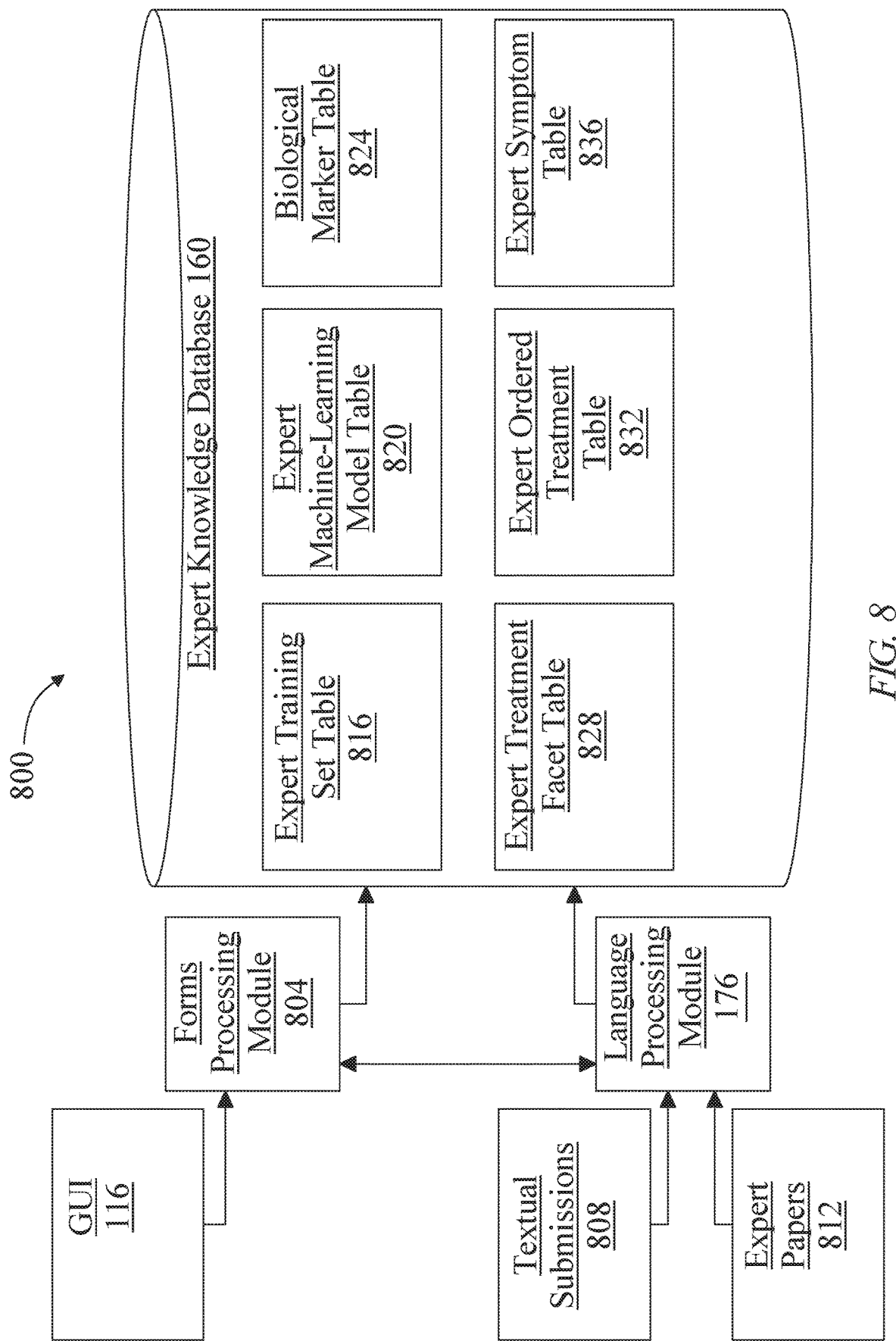
FIG. 8 is a block diagram illustrating an exemplary embodiment of an expert database.

Referring now to FIG. 8, an exemplary embodiment of expert database 164 is illustrated. Expert database 164 may be implemented as any data structure suitable for use as biological marker database 124 as described above in more detail in reference to FIG. 1. One or more database tables may be linked to one another by, for instance, common column values. For instance, a common column between two tables of expert database 164 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 8, expert database 164 includes a forms processing module 804 that may sort data entered in a submission via graphical user interface 116 by, for instance, sorting data from entries in the graphical user interface 116 to related categories of data; for instance, data entered in an entry relating in the graphical user interface 116 to a biological marker 120 may be sorted into variables and/or data structures for storage of biological marker 120, while data entered in an entry relating to a category of training data and/or an element thereof may be sorted into variables and/or data structures for the storage of, respectively, categories of training data. Where data is chosen by an expert from pre-selected entries such as drop-down lists, data may be stored directly; where data is entered in textual form, language processing module 176 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 176 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 808, such as accomplished by filling out a paper or PDF form and/or submitting narrative information, may likewise be processed using language processing module 176. Data may be extracted from expert papers 812, which may include without limitation publications in medical and/or scientific journals, by language processing module 176 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 8, one or more tables contained within expert database 164 may include expert training set table 816; expert training set table 816 may include one or more expert inputs regarding training sets. One or more tables contained within expert database 164 may include expert machine-learning model table 820; expert machine-learning model table 820 may include one or more expert inputs regarding machine-learning models. One or more tables contained within expert database 164 may include biological marker 120 table 824; biological marker 120 table 824 may include one or more expert inputs regarding biological marker 120. One or more tables contained within expert database 164 may include expert treatment facet table 828; expert treatment facet table 828 may include one or more expert inputs regarding treatment facets. One or more tables contained within expert database 164 may include expert ordered treatment table 832; expert ordered treatment table 832 may include one or more expert inputs regarding ordered treatment. One or more tables contained within expert database 164 may include expert symptom table 836; expert symptom table 836 may include one or more expert inputs regarding symptoms.

Referring now to FIG. 9, an exemplary embodiment 900 of treatment training set is illustrated. Treatment training set includes a plurality of data entries 904. Each data entry 904 contains a comprehensive diagnosis 908 correlated to one or more prioritized treatment facets. In an embodiment, a comprehensive diagnosis 908 may be correlated to a first prioritized treatment facet 912. In an embodiment, a comprehensive diagnosis 908 may be correlated to a second prioritized treatment facet 916. In an embodiment, a comprehensive diagnosis 908 may be correlated to a third prioritized treatment facet 920. In an embodiment, a comprehensive diagnosis 908 may be correlated to a fourth prioritized treatment facet 924. In an embodiment, a comprehensive diagnosis 908 may be correlated to a fifth prioritized treatment facet 928. In an embodiment, a comprehensive diagnosis 908 may be correlated to a Nth prioritized treatment facet 932. For instance and without limitation, treatment training set 148 may contain a data entry 904 containing a comprehensive diagnosis 908 such as rheumatoid arthritis that may be correlated to a first prioritized treatment facet 912 initiate gluten free diet, a second prioritized treatment facet 916 heal the gut, a third prioritized treatment facet 920 find and treat infections, a fourth prioritized treatment facet 924 test for heavy metals, a fifth prioritized treatment facet 928 test for mycotoxins, and an Nth prioritized treatment facet support the immune system.

Figure 10:
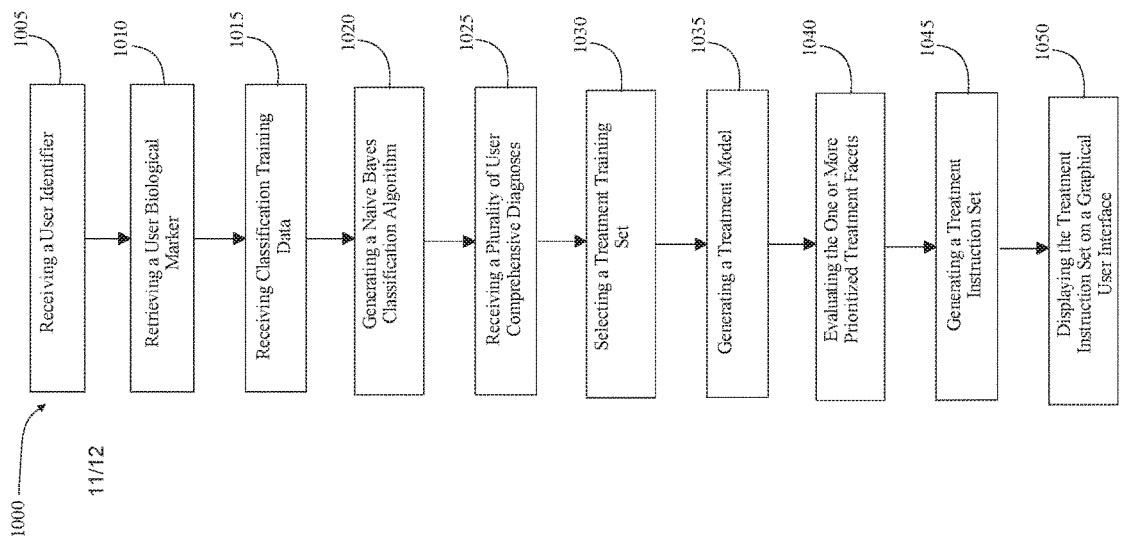
FIG. 10 is a process flow diagram illustrating an exemplary embodiment of a method for prioritizing comprehensive diagnoses.

Referring now to FIG. 10, an exemplary embodiment of a method 1000 of prioritizing comprehensive diagnoses is illustrated. At step 1005 a processor receives a user identifier 112 entered by a comprehensive advisor located on a graphical user interface 116 operating on the processor. A user identifier 112 includes any of the user identifier 112 as described above in reference to FIG. 1. For instance and without limitation, a user identifier 112 may include a piece of information identifying a particular user such as a user's name or date of birth. Comprehensive advisor includes any of the comprehensive advisors as described above in reference to FIG. 1. For instance and without limitation, comprehensive advisor may include a functional medicine doctor, nurse practitioner, physician assistant and the like. In an embodiment, comprehensive advisor may enter a user identifier 112 on graphical user interface 116 and more information pertaining to a user may be retrieved from a user database. User database may include background information about a user such as a user's demographics, previous medical history, and the like.

With continued reference to FIG. 10, at step 1010 a processor retrieves a user biological marker 120 from a biological marker database 124 as a function of a user identifier 112. User biological marker 120 includes any of the user biological marker 120 as described above in reference to FIG. 1. Biological marker database 124 may contain biological marker 120 pertaining to a user as described above in reference to FIGS. 1-9. Processor may retrieve a biological marker 120 from biological marker database 124 by matching the user identifier 112 receive from comprehensive advisor to a user identifier 112 stored within biological marker database 124. For instance and without limitation, processor may match a user's name and address entered by comprehensive advisor on graphical user interface 116 to a user's name and address stored within biological marker database 124 to ensure that contain the same information. Processor may retrieve a particular user biological marker 120 based on input from comprehensive advisor located on graphical user interface 116. For example, user identifier 112 entered by comprehensive advisor may specify a particular biological extraction to retrieve or a particular time period to retrieve a stored biological marker 120 from.

With continued reference to FIG. 10, at step 1015 a processor receives classification training data 128 wherein classification training data 128 contains a plurality of data entries including biological marker 120 data containing alert and non-alert classification labels. Classification training data 128 may include any of the classification training data 128 as described above in reference to FIGS. 1-9. Classification training data 128 may be generated and received based on expert input as described above in more detail in reference to FIGS. 1-9. Classification training data 128 may be received from expert database 164 and/or training set database 152.

With continued reference to FIG. 10, at step 1020 a processor generates a naïve Bayes classification algorithm utilizing classification training data 128 wherein the naïve Bayes classification algorithm utilizes the user biological marker 120 as an input and outputs a biological marker classification label 136. Generating a naïve Bayes classification algorithm may be performed utilizing any of the methods as described above in reference to FIGS. 1-9. Biological marker classification label 136 includes any of the biological marker classification label 136s as described above in reference to FIGS. 1-9. In an embodiment, biological marker classification label 136 may contain a classifier indicator of an alert or non-alert. For instance and without limitation, naïve Bayes classification algorithm may generate a biological marker classification label 136 for a biological maker such as a serum fasting blood glucose level that contains an alert biological marker classification label 136 while a urinary glucose level that contains a non-alert biological marker classification label 136.

With continued reference to FIG. 10, at step 1025 a processor receives a plurality of user comprehensive diagnoses 144 entered by a comprehensive advisor on a graphical user interface 116 operating on the processor. A plurality of comprehensive diagnoses may include any of the comprehensive diagnoses as described above in reference to FIGS. 1-10. In an embodiment, comprehensive advisor may select one or more comprehensive diagnoses displayed on a graphical user interface 116 pertaining to a user. In yet another non-limiting example, one or more comprehensive diagnoses pertaining to a user may be stored within user database. User database is described above in more detail in reference to FIGS. 1-10. In an embodiment, a processor may display one or more comprehensive diagnoses retrieved from user database, whereby comprehensive advisor may select one or more comprehensive diagnoses on graphical user interface 116 by highlighting one or more that are displayed or touching the screen surface on the graphical user interface 116. In yet another non-limiting example, comprehensive advisor may enter in free form textual input boxes one or more comprehensive diagnoses at graphical user interface 116. In yet another non-limiting example, comprehensive advisor may select one or more comprehensive diagnoses from a drop down list displayed on graphical user interface 116.

With continued reference to FIG. 10, at step 1030 a processor selects a treatment training set 148 as a function of a biological marker classification label 136 wherein the treatment training set 148 includes a plurality of data entries containing comprehensive diagnoses correlated to one or more prioritized treatment facets. Treatment training set 148 may include any of the treatment training set 148 as described above in reference to FIGS. 1-9. A processor may select a treatment training set 148 that contains a classifier label that matches a biological marker classification label 136. For instance and without limitation, a processor may select a treatment training set 148 from training set database 152 that contains a classifier label such as "alert" that matches a biological marker classification label 136 such as "alert." Treatment training set 148 may be organized within training set database 152 according to classification labels as described above in more detail in reference to FIGS. 1-9.

With continued reference to FIG. 10, selecting a treatment training set 148 may be performed by generating classification algorithms by a processor. In an embodiment, a processor may receive diagnostic training data where the diagnostic training data includes a plurality of data entries containing comprehensive diagnoses containing urgent and non-urgent labels. Diagnostic training data may include any of the diagnostic training data as described above in reference to FIGS. 1-9. A processor generates a classification algorithm utilizing the diagnostic training data wherein the classification algorithm utilizes a plurality of user comprehensive diagnoses 144 as inputs and outputs a comprehensive diagnosis classification label for each of the plurality of user comprehensive diagnoses 144. For instance and without limitation, a comprehensive diagnosis such as Lyme Disease may contain an urgent classification label while a comprehensive diagnosis such as osteoarthritis may contain a non-urgent classification label. Classification algorithm includes any of the classification algorithms as described above in reference to FIGS. 1-9. A processor selects a treatment training set 148 as a function of a comprehensive diagnosis classification label for each of the plurality of user comprehensive diagnoses 144. In an embodiment, processor may match a comprehensive diagnosis classification label to a treatment training set 148 classifier label. For example, a comprehensive diagnosis classification label that contains an urgent label may be matched to a treatment training set 148 contained within training set database 152 that contains an urgent classifier label.

With continued reference to FIG. 10, at step 1035 a processor generates using a supervised machine-learning model a treatment model 156 that outputs an ordered priority treatment list for each of the plurality of comprehensive diagnoses utilizing the selected treatment training set. Supervised machine-learning model includes any of the supervised machine-learning models as described above in reference to FIGS. 1-10. Treatment model 156 includes any of the treatment model 156 as described above in reference to FIGS. 1-10. Treatment model 156 may include an algorithm, mathematical expression, series of calculations and the like as described above in more detail. Ordered priority treatment list includes any of the ordered priority treatment list as described above in reference to FIGS. 1-9. For instance and without limitation, a treatment model 156 may be utilized to generate an ordered priority treatment list for a comprehensive diagnosis such as system *Candida Albicans* that includes an ordered priority treatment list that contains treatments that consist of first eliminating sugar from diet, second following a yeast free diet, third initiating a caprylic acid supplement regimen, fourth initiating a garlic supplement regimen, and fifth initiating a meditation practice.

With continued reference to FIG. 10, at step 1040 a processor evaluates one or more prioritized treatment facets contained within an ordered priority treatment list for a plurality of comprehensive diagnosis. Evaluating one or more prioritized treatment facets may include combining and eliminating one or more prioritized treatment facets relating to one or more comprehensive diagnoses. For example, evaluating one or more treatment facets may include examining a first comprehensive diagnosis such as broken ankle that contains a first treatment facet of ice, a second treatment facet of calcium supplementation, and a third treatment facet of rest. A processor may evaluate the treatment facets for the broken ankle as compared to treatment facets for a second comprehensive diagnosis such as myocardial infarction that contains a first treatment facet of following an anti-inflammatory diet and a second treatment facet that includes consuming a fish oil supplement. A processor may then evaluate all five total treatment facets to find any duplicates or any facets that may contraindicate one another and generate an ordered treatment plan that contains all five treatment facets in a prioritized order. A processor may determine how a treatment facet given a first priority for a first comprehensive diagnosis relates to a treatment facet given a first priority for a second comprehensive diagnosis. Evaluating may include determining which prioritized treatment facet for a plurality of comprehensive diagnoses will be placed in what order in treatment instruction set. This may be determined based on expert input such as what may be contained within expert knowledge database.

With continued reference to FIG. 10, evaluating one or more treatment facets may include correlating any user symptom data to one or more comprehensive diagnoses to determine the final order of treatment facets from one or more comprehensive diagnoses. A processor may retrieve an element of user symptom data from user data. An element of user symptom data may include any of the elements of user symptom data as described above in reference to FIGS. 1-9. A processor may correlate an element of user symptom data to a comprehensive diagnosis. Correlation may be performed utilizing any method as described above in reference to FIGS. 1-9. A processor may generate an ordered treatment instruction set 172 as a function of an element of user symptom data correlated to a comprehensive diagnosis. For example, a particular comprehensive diagnosis that has one or more elements of user symptom data correlated to it, may be utilized by a processor to generate an ordered treatment plan that contains one or more treatment facets related to the particular comprehensive diagnosis to be placed ahead of other treatment facets relating to other comprehensive diagnoses that do not contain any elements of user symptom data correlated to them.

With continued reference to FIG. 10, at step 1045 a processor generates a treatment instruction set 172 wherein the treatment instruction set 172 includes an ordered treatment plan containing one or more combined prioritized treatment facets for a plurality of comprehensive diagnoses. Generating an ordered treatment plan may be done utilizing any of the methods as described above in reference to FIGS. 1-10. Generating an ordered treatment plan may include receiving input from a comprehensive advisor. In an embodiment, a processor may receive a comprehensive input descriptor generated by a comprehensive advisor on a graphical user interface 116 located on the processor. Comprehensive input descriptor includes any of the comprehensive input descriptors as described above in reference to FIGS. 1-9. In an embodiment, comprehensive input descriptor may be stored locally such as within expert database 164. Comprehensive input descriptor includes an advisor interaction summary which may contain details describing a particular encounter between a user and a comprehensive advisor as described above in more detail. For example, an advisor interaction summary may include a description of progress a user may be making with a particular comprehensive diagnosis and may aid processor in selecting a first treatment facet to be placed in a first position within treatment instruction set. In yet another non-limiting example, a particular advisor interaction summary may contain a description from a physical examination of a user by a comprehensive advisor and may dictate what treatment facet needs to be addressed first.

With continued reference to FIG. 10, generating a treatment instruction set 172 may include utilizing user inputs relating to short term and long term target indicators to select a first treatment facet and a last treatment facet in an ordered priority. A processor may retrieve a user diagnostic factor input from user database wherein the user diagnostic factor input includes a long-term target indicator and short-term target indicator. Diagnostic factor input may include any of the diagnostic factor input as described above in more detail in reference to FIGS. 1-10. A processor may generate a loss function utilizing the user diagnostic factor input and minimize the loss function. This may be performed utilizing any of the methods as described above in reference to FIGS. 1-10. A processor may then generate an ordered treatment plan as a function of minimizing the loss function. For example, a particular treatment facet may be placed in last place within treatment instruction set 172 that fulfills a particular long-term target indicator while a particular treatment facet that fulfills a user's short-term target indicator may be placed in first place within treatment instruction set. Treatment instruction set 172 may also be generated based on calculating a comprehensive diagnosis impact score. Comprehensive diagnosis impact score may include factor scores generated by users, comprehensive advisors, and expert input that may help dictate placement of treatment facets in a particular order within treatment instruction set 172 based on factors that include how difficult a particular treatment facet may be to implement, what types of resources and how many resources a user may have to use to fulfill a particular treatment facet, as well as how much effort a user may be willing to complete a particular treatment facet. Factors may be given numerical scores as described above in more detail in reference to FIGS. 1-9.

With continued reference to FIG. 10, generating treatment instruction set 172 may include placing treatment facets in a particular order as a function of a treatment facets priority for a particular comprehensive diagnosis as well as a treatment facets priority as compared to other treatment facets within treatment instruction set. For example, generating an ordered treatment plan may include selecting a first treatment facet as a function of a first priority treatment, selecting a second treatment facet as a function of the first treatment facet, and selecting a third treatment facet as a function of the second treatment facet. In yet another non-limiting example, a first treatment facet may be selected as a function of a first priority treatment, a second treatment facet may be selected as a function of the first priority treatment, and a third treatment facet may be selected as a function of the second priority treatment.

With continued reference to FIG. 10, at step 1050 a processor displays a treatment instruction set 172 on a graphical user interface 116 located on a processor. A treatment instruction set 172 may be displayed utilizing any methods as described herein. In an embodiment, a treatment instruction set 172 may be displayed on a graphical user interface 116 so that a comprehensive advisor can select a particular treatment facet to obtain more detailed information about that particular treatment facet and what treatment for that particular treatment facet includes. For example, a particular treatment facet such as "initiating a multi-vitamin supplement regimen" may provide more detailed information such as potential recommended supplements for a user based on a user's age, sex, medical history, concurrent comprehensive diagnoses, as well as other medications and supplements that a user may be taking. In yet another non-limiting example, a particular facet such as "start treatment with rifaximin" may contain additional information for the comprehensive diagnosis such as the ideal dose for a user based on a user's age, sex, height, weight, other medication conditions, health history, drug allergies and the like.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
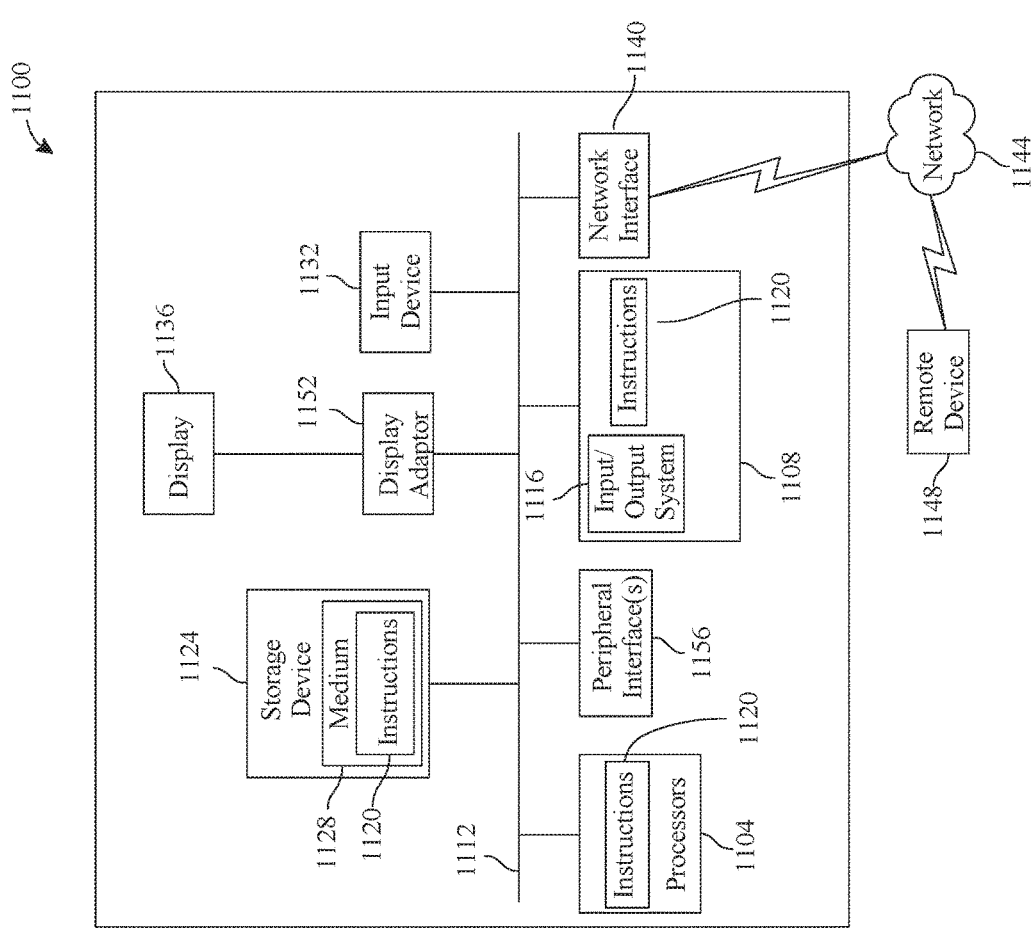
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Memory 1108 may include various components (e.g., machine-readable media) including, but not limited to, a random access memory component, a read only memory component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for prioritizing comprehensive diagnoses, the system comprising:
   at least a processor coupled to a memory, wherein the at least a processor further comprises:
   a classification module, the classification module designed and configured to:
   receive by a graphical user interface operating on the at least a processor a user identifier entered by a comprehensive advisor;
   retrieve a user biological marker from a biological marker database as a function of the user identifier;
   receive classification training data wherein the classification training data contains a plurality of data entries including biological marker data containing alert and non-alert classification labels; and
   generate a naïve Bayes classification algorithm utilizing classification training data wherein the naïve Bayes classification algorithm utilizes the user biological marker as an input and outputs a biological marker classification label; and
   a priority treatment module, the priority treatment module designed and configured to:
   receive the biological marker classification label from the classification module;
   receive by the graphical user interface operating on the at least a processor a plurality of user comprehensive diagnoses entered by the comprehensive advisor;
   receive by the graphical user interface operating on the at least a processor a domain restriction entered by the comprehensive advisor;
   select a treatment training set as a function of the biological marker classification label wherein the treatment training set includes a plurality of data entries containing comprehensive diagnoses correlated to one or more prioritized treatment facets generate, using a supervised machine-learning algorithm, a treatment model that outputs an ordered priority treatment list for each of the plurality of comprehensive diagnoses utilizing the selected treatment training set, said ordered priority treatment list detailing an order in which the comprehensive diagnoses should be treated, wherein generating the treatment model further comprises:

configuring the supervised machine-learning algorithm to apply the domain restriction to the selected training data;

evaluate the one or more prioritized treatment facets contained within the ordered priority treatment list for the plurality of comprehensive diagnoses;

generate a treatment instruction set wherein the treatment instruction set further comprises generating an ordered treatment plan containing one or more combined prioritized treatment facets for the plurality of comprehensive diagnoses; and display by the graphical user interface located on the at least a processor the treatment instruction set.

2. The system of claim 1, wherein selecting a treatment training set further comprises selecting a treatment training set containing a classifier label that matches the biological marker classification label.

3. The system of claim 1, wherein receiving a plurality of user comprehensive diagnoses further comprises:

receiving diagnostic training data wherein the diagnostic training data contains a plurality of data entries including comprehensive diagnoses containing urgent and non-urgent labels;

generating a classification algorithm utilizing diagnostic training data wherein the classification algorithm utilizes the plurality of user comprehensive diagnoses as input and outputs a comprehensive diagnosis classification label for each of the plurality of user comprehensive diagnoses; and selecting a treatment training set as a function of the comprehensive diagnosis classification label for each of the plurality of user comprehensive diagnoses.

4. The system of claim 3 further comprising generating a treatment instruction set as a function of the comprehensive diagnosis classification label for each of the plurality of user comprehensive diagnoses.

5. The system of claim 1, wherein evaluating the ordered priority treatment list further comprises:

retrieving an element of user symptom data from a user database;

correlating the element of user symptom data to a comprehensive diagnosis; and generating an ordered treatment instruction set as a function of the element of user symptom data correlated to the comprehensive diagnosis.

6. The system of claim 1, wherein generating a treatment instruction set further comprises:

receiving a comprehensive input descriptor generated by the comprehensive advisor on the graphical user interface located on the at least a processor wherein the comprehensive input descriptor contains an advisor interaction summary; and generating an ordered treatment plan for the plurality of comprehensive diagnoses as a function of the comprehensive input descriptor.

7. The system of claim 1, wherein generating a treatment instruction set further comprises:

retrieving a user diagnostic factor input from a user database wherein the user diagnostic factor input includes a long-term target indicator and a short-term target indicator;

generating a loss function utilizing the user diagnostic factor input;

minimizing the loss function; and generating an ordered treatment plan as a function of minimizing the loss function.

8. The system of claim 1, wherein generating a treatment instruction set further comprises calculating a comprehensive diagnosis impact score wherein the comprehensive diagnosis impact score includes a difficulty factor multiplied by an alimentary standard factor multiplied by an implementation factor.

9. The system of claim 1, wherein generating an ordered treatment plan further comprises:

selecting a first treatment facet as a function of a first priority treatment of the ordered priority treatment list;

selecting a second treatment facet as a function of the first treatment facet; and selecting a third treatment facet as a function of the second treatment facet.

10. The system of claim 1, wherein generating an ordered treatment plan further comprises:

selecting a first treatment facet as a function of a first priority treatment of the ordered priority treatment list;

selecting a second treatment facet as a function of the first priority treatment of the ordered priority treatment list; and selecting a third treatment facet as a function of the second priority treatment of the ordered priority treatment list.

11. A method of prioritizing comprehensive diagnoses, the method comprising:

receiving by at least a processor on a graphical user interface operating on the at least a processor a user identifier entered by a comprehensive advisor;

retrieving by the at least a processor a user biological marker from a biological marker database as a function of the user identifier;

receiving by the at least a processor classification training data wherein the classification training data contains a plurality of data entries including biological marker data containing alert and non-alert classification labels;

generating by the at least a processor a naïve Bayes classification algorithm utilizing classification training data wherein the naïve Bayes classification algorithm utilizes the user biological marker as an input and outputs a biological marker classification label;

receiving by the at least a processor on a graphical user interface operating on the at least a processor a plurality of user comprehensive diagnoses entered by a comprehensive advisor;

receiving by the graphical user interface operating on the at least a processor a domain restriction entered by the comprehensive advisor;

selecting by the at least a processor a treatment training set as a function of the biological marker classification label wherein the treatment training set includes a plurality of data entries containing comprehensive diagnoses correlated to one or more prioritized treatment facets;

generating by the at least a processor using a supervised machine-learning model a treatment model that outputs an ordered priority treatment list for each of the plurality of comprehensive diagnoses utilizing the selected treatment training set, said ordered priority treatment list detailing an order in which the comprehensive diagnoses should be treated, wherein generating the treatment model further comprises:

configuring the supervised machine-learning algorithm to apply the domain restriction to the selected training data;

evaluating by the at least a processor the one or more prioritized treatment facets contained within the ordered priority treatment list for the plurality of comprehensive diagnoses;

generating by the at least a processor a treatment instruction set wherein the treatment instruction set further comprises generating an ordered treatment plan containing one or more combined prioritized treatment facets for the plurality of comprehensive diagnoses; and displaying by the at least a processor on a graphical user interface located on the at least a processor the treatment instruction set.

12. The method of claim 11, wherein selecting a treatment training set further comprises selecting a treatment training set containing a classifier label that matches the biological marker classification label.

13. The method of claim 11, wherein receiving a plurality of user comprehensive diagnoses further comprises:

receiving diagnostic training data wherein the diagnostic training data contains a plurality of data entries including comprehensive diagnoses containing urgent and non-urgent labels;

generating a classification algorithm utilizing diagnostic training data wherein the classification algorithm utilizes the plurality of user comprehensive diagnoses as input and outputs a comprehensive diagnosis classification label for each of the plurality of user comprehensive diagnoses; and selecting a treatment training set as a function of the comprehensive diagnosis classification label for each of the plurality of user comprehensive diagnoses.

14. The method of claim 13 further comprising generating a treatment instruction set as a function of the comprehensive diagnosis classification label for each of the plurality of user comprehensive diagnoses.

15. The method of claim 11, wherein evaluating the ordered priority treatment list further comprises:

retrieving an element of user symptom data from a user database;

correlating the element of user symptom data to a comprehensive diagnosis; and generating an ordered treatment instruction set as a function of the element of user symptom data correlated to the comprehensive diagnosis.

16. The method of claim 11, wherein generating a treatment instruction set further comprises:

receiving a comprehensive input descriptor generated by a comprehensive advisor on a graphical user interface located on the at least a processor wherein the comprehensive input descriptor contains an advisor interaction summary; and generating an ordered treatment plan for the plurality of comprehensive diagnoses as a function of the comprehensive input descriptor.

17. The method of claim 11, wherein generating a treatment instruction set further comprises:

retrieving a user diagnostic factor input from a user database wherein the user diagnostic factor input includes a long-term target indicator and a short-term target indicator;

generating a loss function utilizing the user diagnostic factor input;

minimizing the loss function; and generating an ordered treatment plan as a function of minimizing the loss function.

18. The method of claim 11, wherein generating a treatment instruction set further comprises calculating a comprehensive diagnosis impact score wherein the comprehensive diagnosis impact score includes a difficulty factor multiplied by an alimentary standard factor multiplied by an implementation factor.

19. The method of claim 11, wherein generating an ordered treatment plan further comprises:

selecting a first treatment facet as a function of a first priority treatment of the ordered priority treatment list;

selecting a second treatment facet as a function of the first treatment facet; and selecting a third treatment facet as a function of the second treatment facet.

20. The method of claim 11, wherein generating an ordered treatment plan further comprises:

selecting a first treatment facet as a function of a first priority treatment of the ordered priority treatment list;

selecting a second treatment facet as a function of the first priority treatment of the ordered priority treatment list; and selecting a third treatment facet as a function of the second priority treatment of the ordered priority treatment list.

* * * * *